(12) United States Patent
Huang et al.

(10) Patent No.: US 11,786,523 B2
(45) Date of Patent: Oct. 17, 2023

(54) COMPOSITION AND METHOD FOR REDUCING THROMBOCYTOPENIA

(71) Applicant: BEYONDSPRING PHARMACEUTICALS, INC., New York, NY (US)

(72) Inventors: Lan Huang, New York, NY (US); Ramon Mohanlal, New York, NY (US); George Kenneth Lloyd, New York, NY (US)

(73) Assignee: BEYONDSPRING PHARMACEUTICALS, INC., New York, NY (US)

( * ) Notice: Subject to any disclaimer, the term of this patent is extended or adjusted under 35 U.S.C. 154(b) by 105 days.

(21) Appl. No.: 16/964,401

(22) PCT Filed: Jan. 23, 2019

(86) PCT No.: PCT/US2019/014673
§ 371 (c)(1),
(2) Date: Jul. 23, 2020

(87) PCT Pub. No.: WO2019/147615
PCT Pub. Date: Aug. 1, 2019

(65) Prior Publication Data
US 2021/0046068 A1 Feb. 18, 2021

Related U.S. Application Data

(60) Provisional application No. 62/718,814, filed on Aug. 14, 2018, provisional application No. 62/621,543, filed on Jan. 24, 2018.

(51) Int. Cl.
*A61K 31/496* (2006.01)
*A61P 7/02* (2006.01)
*A61K 31/7068* (2006.01)

(52) U.S. Cl.
CPC ........ *A61K 31/496* (2013.01); *A61K 31/7068* (2013.01); *A61P 7/02* (2018.01)

(58) Field of Classification Search
CPC .............................. A61K 31/496; A61P 7/02
See application file for complete search history.

(56) References Cited

U.S. PATENT DOCUMENTS

| | | |
|---|---|---|
| 4,535,183 A | 8/1985 | Kneen |
| 5,607,934 A | 3/1997 | Tone et al. |
| 5,852,018 A | 2/1998 | Rhodes |
| 5,733,888 A | 12/1998 | Bryans et al. |
| 5,872,151 A | 2/1999 | Rhodes |
| 5,874,443 A | 2/1999 | Kiely et al. |
| 5,886,210 A | 3/1999 | Rayle et al. |
| 5,891,877 A | 4/1999 | Brocchini et al. |
| 5,922,683 A | 7/1999 | Or et al. |
| 5,939,098 A | 8/1999 | Reidenberg et al. |
| 5,958,980 A | 9/1999 | Rhodes |
| 6,069,146 A | 5/2000 | Fenical et al. |
| 6,096,786 A | 8/2000 | Rhodes |
| 6,350,759 B1 | 2/2002 | Casara et al. |
| 6,358,957 B1 | 3/2002 | Fukumoto et al. |
| 6,500,825 B2 | 12/2002 | Lan et al. |
| 6,506,787 B2 | 1/2003 | Fujishita et al. |
| 6,509,331 B1 | 1/2003 | Audia et al. |
| 6,583,143 B2 | 6/2003 | Haddach |
| 6,713,480 B2 | 3/2004 | Fukumoto et al. |
| 6,808,710 B1 | 10/2004 | Wood et al. |
| 6,972,289 B1 | 12/2005 | Kanzaki et al. |
| 7,026,322 B2 | 4/2006 | Hayashi et al. |
| 7,064,201 B2 | 6/2006 | Hayashi et al. |
| 7,488,802 B2 | 2/2009 | Collins et al. |
| 7,629,380 B2 | 12/2009 | McMorris et al. |
| 7,635,757 B2 | 12/2009 | Freeman et al. |
| 7,674,903 B2 | 3/2010 | Hayashi et al. |
| 7,700,615 B2 | 4/2010 | Edwards et al. |
| 7,919,497 B2 | 4/2011 | Palladino et al. |
| 7,935,704 B2 | 5/2011 | Palladino et al. |
| 7,943,743 B2 | 5/2011 | Korman et al. |
| 7,956,058 B2 | 6/2011 | Hayashi et al. |
| 8,008,449 B2 | 8/2011 | Korman et al. |
| 8,129,527 B2 | 3/2012 | Palladino et al. |
| 8,168,757 B2 | 5/2012 | Finnefrock et al. |
| 8,217,149 B2 | 7/2012 | Irving et al. |
| 8,247,552 B2 | 8/2012 | Palladino et al. |
| 8,618,292 B2 | 12/2013 | Palladino et al. |
| 9,358,289 B2 | 6/2016 | Korman et al. |
| 9,394,368 B2 | 7/2016 | Brogdon et al. |
| 10,076,518 B2 | 9/2018 | Huang |
| 10,155,748 B2 | 12/2018 | Huang et al. |
| 10,238,650 B2 | 3/2019 | Huang |
| 10,357,491 B2 | 7/2019 | Huang |
| 10,550,104 B2 | 2/2020 | Huang et al. |
| 10,569,169 B2 | 2/2020 | Li et al. |
| 10,596,169 B2 | 3/2020 | Huang |
| 10,668,063 B2 | 6/2020 | Huang |

(Continued)

FOREIGN PATENT DOCUMENTS

| | | |
|---|---|---|
| CN | 110240592 | 9/2017 |
| EA | 010198 B1 | 6/2008 |
| EA | 016817 B1 | 7/2012 |
| EP | 0 054 924 | 6/1982 |
| EP | 0 655 060 | 1/1998 |
| GB | 2143823 | 2/1985 |
| JP | 05-9164 | 1/1993 |
| JP | 05-255106 | 10/1993 |
| JP | 10-130266 | 5/1998 |
| JP | 2002-507612 A | 3/2002 |

(Continued)

OTHER PUBLICATIONS

Ishibashi et al., Blood, 1989, 74(4) p. 1241-1244. (Year: 1989).*
Weycker et al., BMC Cancer, 2019, 19, Article No. 151, 8 pgs. (Year: 2019).*
Millward et al., Invest. New Drugs, 2012, 30, p. 1065-1073. (Year: 2012).*

(Continued)

*Primary Examiner* — Jonathan S Lau
(74) *Attorney, Agent, or Firm* — Knobbe, Martens, Olson & Bear, LLP

(57) ABSTRACT

Disclosed herein are methods of reducing or preventing thrombocytopenia, in a clinically relevant manner, that is caused by chemotherapy or radiation therapy by administering plinabulin to a subject.

31 Claims, 5 Drawing Sheets

(56) References Cited

U.S. PATENT DOCUMENTS

| | | |
|---|---|---|
| 2002/0028819 A1 | 3/2002 | Teng et al. |
| 2002/0143021 A1 | 10/2002 | Fukumoto et al. |
| 2004/0102454 A1 | 5/2004 | Hayashi et al. |
| 2004/0176372 A1 | 9/2004 | Suto et al. |
| 2006/0079534 A1 | 4/2006 | Kanzaki et al. |
| 2006/0167010 A1 | 7/2006 | Hayashi et al. |
| 2006/0223822 A1 | 10/2006 | Hayashi et al. |
| 2007/0293453 A1 | 12/2007 | Fisher et al. |
| 2008/0199485 A1 | 8/2008 | Kundig et al. |
| 2008/0255035 A1 | 10/2008 | Trieu et al. |
| 2009/0170837 A1 | 7/2009 | Gourdeau et al. |
| 2009/0317368 A1 | 12/2009 | Chen |
| 2012/0041070 A1 | 2/2012 | Shengfan et al. |
| 2012/0277251 A1 | 11/2012 | Palladino et al. |
| 2013/0131018 A1 | 5/2013 | Leblond et al. |
| 2013/0303481 A1 | 11/2013 | Marcus |
| 2014/0322275 A1 | 10/2014 | Brogdon et al. |
| 2015/0202291 A1 | 7/2015 | Bosch et al. |
| 2015/0291549 A1 | 10/2015 | Chupak et al. |
| 2016/0243153 A1 | 8/2016 | Sundaram et al. |
| 2016/0250209 A1* | 9/2016 | Huang .............. A61K 31/496 514/254.05 |
| 2017/0226221 A1 | 8/2017 | Madiyalakan et al. |
| 2018/0028531 A1 | 2/2018 | Huang et al. |
| 2018/0140600 A1 | 5/2018 | Li et al. |
| 2019/0175587 A1 | 6/2019 | Huang et al. |
| 2019/0380983 A1 | 12/2019 | Mohanlal |
| 2020/0038395 A1 | 2/2020 | Mohanlal |
| 2020/0129504 A1 | 4/2020 | Mohanlal et al. |
| 2020/0237754 A1 | 7/2020 | Huang |
| 2020/0277280 A1 | 9/2020 | Huang |
| 2020/0281921 A1 | 9/2020 | Huang |
| 2020/0289503 A1 | 9/2020 | Huang |
| 2021/0030843 A1 | 2/2021 | Mohanlal |
| 2021/0161844 A1 | 6/2021 | Mohanlal et al. |
| 2021/0161888 A1 | 6/2021 | Huang et al. |
| 2021/0177952 A1 | 6/2021 | Mohanlal et al. |
| 2021/0275524 A1 | 9/2021 | Huang |

FOREIGN PATENT DOCUMENTS

| | | |
|---|---|---|
| JP | 2012-144512 | 8/2012 |
| JP | 2013-501791 | 1/2013 |
| JP | 2016-516523 | 6/2016 |
| RU | 2258702 | 8/2005 |
| RU | 2011 148 945 A | 4/2010 |
| WO | WO 87/05297 | 9/1987 |
| WO | WO 94/07479 | 4/1994 |
| WO | WO 95/06077 | 3/1995 |
| WO | WO 95/21832 | 8/1995 |
| WO | WO 96/20190 | 7/1996 |
| WO | WO 99/38844 | 8/1999 |
| WO | WO 99/048889 | 9/1999 |
| WO | WO 00/012121 | 3/2000 |
| WO | WO 01/053290 | 7/2001 |
| WO | WO 01/070663 | 9/2001 |
| WO | WO 03/074550 | 9/2003 |
| WO | WO 03/097164 | 11/2003 |
| WO | WO 04/016600 | 2/2004 |
| WO | WO 04/054498 | 7/2004 |
| WO | WO 04/093831 | 11/2004 |
| WO | WO 05/077940 | 8/2005 |
| WO | WO 06/121168 | 11/2006 |
| WO | WO 07/035841 | 3/2007 |
| WO | WO 07/113648 | 10/2007 |
| WO | WO 08/128169 | 10/2008 |
| WO | WO 09/089260 | 7/2009 |
| WO | WO 10/001169 | 1/2010 |
| WO | WO 10/083439 | 7/2010 |
| WO | WO 11/034954 | 3/2011 |
| WO | WO 11/050344 | 5/2011 |
| WO | WO 11/066389 | 6/2011 |
| WO | WO 11/079507 | 7/2011 |
| WO | WO 11/109625 | 9/2011 |
| WO | WO 11/146382 | 11/2011 |
| WO | WO 11/151423 | 12/2011 |
| WO | WO 12/014549 | 2/2012 |
| WO | WO 12/035436 | 3/2012 |
| WO | WO 12/074904 | 6/2012 |
| WO | WO 12/145493 | 10/2012 |
| WO | WO 13/078537 | 6/2013 |
| WO | WO 13/090552 | 6/2013 |
| WO | WO 13/177633 | 12/2013 |
| WO | WO 14/066834 | 5/2014 |
| WO | WO 14/130657 | 8/2014 |
| WO | WO 14/160183 | 10/2014 |
| WO | WO 14/195852 | 12/2014 |
| WO | WO 15/051543 | 4/2015 |
| WO | WO 15/069770 | 5/2015 |
| WO | WO 15/069790 | 5/2015 |
| WO | WO 15/160641 | 10/2015 |
| WO | WO 16/144635 | 9/2016 |
| WO | WO 16/144636 | 9/2016 |
| WO | WO 16/0165007 | 10/2016 |
| WO | WO 17/062505 | 4/2017 |
| WO | WO 18/129381 | 7/2018 |
| WO | WO 21/225908 | 11/2021 |

OTHER PUBLICATIONS

Definition of prevent, Oxford English Dictionary Online, http://dictionary.oed.com/, accessed online Mar. 27, 2010, especially definition 9a. at p. 2. (Year: 2010).*

Buchbinder et al., Feb. 2016, CTLA-4 and PD-1 pathways: similarities, differences, and implications of their inhibition, American Journal of Clinical Oncology, 39(1):98-106.

ClinicalTrials.gov Identifier NCT03294577, "Plinabulin vs. pegfilgrastim in prevention of TAC induced neutropenia" (Sep. 27, 2107). <URL:ttps://clinicaltrials.gov/ct2/show/NCT3294577> 4 pp.

Crawford, Aug. 2003, Once-per-cycle pegilgrastim (neulata) for the management of chemotherapy-induced neutropenia, Seminars in Oncology 30(4)Suppl 13:23-30.

Dale, Oct. 2015, Neutropenia, John Wiley & Sons Ltd., www.els.net, 8 pp.

Dalgleish, 2015, Rationale for combining immunotherapy with chemotherapy, Immunotherapy, 7(3):309-316.

Das et al., Feb. 1, 2015, Combination therapy with anti-CLTA4 and antiPD1 leads to distinct immunologic changes in-vivo, J. Immunolog, 194(3):950-959.

Field et al., 2014, Microtubule-targeting agents are clinically successful due to both mitotic and interphase impairment of microtubule function, Bioorganic & Medicinal Chemistry, 22:5050-5059.

Folkman, Dec. 2002, Role of angiogenesis in tumor growth and metastasis, Semin Oncol, 29:15-18.

Hellmann et al., Nov. 21, 2019, Nivolumab plus imipimumab in advanced non-small-cell lung cancer, The New England Journal of Medicine, 381:2020-2031.

Hodi et al., Nov. 2016, Combined nivolumab and ipilimumab versus ipilimumab alone in patients with advanced melanoma: 2-year overall survival outcomes in a multicentre, randomised, controlled, phase 2 trial, Lancet Oncol., 17:1558-1568.

Intlekofer et al., Jul. 2013, At the bench: preclinical rationale for CTLA-4 and PD-1 blockade as cancer immunotherapy, J. Leukoc Biol., 94(1):25-39.

Kashyap et al., Sep. 24, 2019, GEF-H1 signaling upon microtubule destabilization is required for dendritic cell activation and specific anti-tumor responses, Cell Reports, 28:3367-3380.

Khramkina, 1077, Workshop on organic synthesis, Publishing House "Chemistry" Leningrad branch, chapter III on pp. 46-60.

Krendel et al., Apr. 2002, Nucleotide exchange factor GEF-H1 mediates cross-talk between microtubules and the actin cytoskeleton, Nature Cell Biology, 4:294-301 and supplementary information.

Li et al., May-Jun. 2017, Epitope mapping reveals the binding mechanism of a functional antibody cross-reactive to both human and murine programmed death 1, MABS, 9(4):628-637.

Lloyd et al., 2015, Abstract A184: Activity of plinabulin in tumor models with kras mutations, Mol. Can. Thera. 14(12):Suppl. 2.

(56) References Cited

OTHER PUBLICATIONS

Melero et al., Aug. 2015, Evolving synergistic combinations of targeted immunotherapies to combat cancer, Nature Reviews Cancer, 15:457-472.

Mohanlal et al., Feb. 10, 2018, Plinabulin, a novel small molecule clinical stage I0 agent with anticancer activity, to prevent chemo-induced neutropenia and immune related AEs, Journal of Clinical Oncology, 36(5 Suppl): 126.

Nabholz, 2001, Phase II study of docetaxel, doxorubiin, and cyclophosphamide as first-line chemotherapy for metastatic breast cancer, Journal of Clinical Oncology, 19:314-321.

Natoli et al., Mar. 3, 2021. Plinabulin, a distinct microtubule-targeting chemotherapy, promotes M1-like macrophage polarization and anti-tumor immunity, Frontiers in Oncology, 11:1-14.

Nielsen et al., Jun. 2005, Alternative splice variants of the human PD-1 gene, Cell Immunol., 235(2):109-116.

PRNewswire.com, Jun. 22, 2010, Nereus Pharmaceuticals completes enrollment of phase 2 advance clinical trial of plinabulin in non-small cell lung cancer, 4 pp.

Rathkopf, Jun. 20, 2008, Phase II trial of docetaxel with rapid androgen cycling for progressive noncastrate prostate cancer, J. Clin. Onc. 26(18):2959-2966.

Riedel et al., Jun. 2007, A phase II trial of carboplatinvinorelbine with pegfilgrastim support for the treatment of patients with advanced non-small ceil lung cancer, Journal of Thoracic Oncology, 2(6):520-525.

Selby et al., Sep. 9, 2016, Preclinical development of ipilimumab and nivolumab combination immunotherapy: mouse tumor models, in vitro functional studies, and cynomolgus macaque toxicology. PloS One, 11(9):e0161779, 19 pp.

Spain et al., Feb. 6, 2016, Management of toxicities of immune checkpoint inhibitors, Cancer Treatment Reviews, 44:51-60.

Vainas, 2012, Personalising docetaxel and G-CSF schedules in cancer patients by a clinically validated computational model, British J. Cancer, 107:814-822.

Wailoo, 2009, The risk of febrile neutropenia in patients with non-small-cell lung cancer treated with docetaxel: a systematic review and meta-analysis, British J. Cancer 100(3):436-441.

Extended European Search Report dated Nov. 17, 2021 in patent application No. 19743897.1.

"Definition of 'within'". [Online] [2015 Archived version accessed on Aug. 13, 2020 from https://web.archive.org/web/20151030162428/https://dictionary.cambridge.org/us/dictionary/english/within. Cambridge English Dictionary. (Year: 2015).

Abels, Christoph, Targeting of the Vascular System of Solid Tumours by Photodynamic Therapy (PDT), Photochem Photobiol Sci., (Mar. 2004) 3: 765-771.

Abolhasani et al., Jan. 2015, In-silico investgation of tubulin binding modes of a series of novel antiproliferative spiroisoxazoline compounds using docking studies, Iranian Journal of Pharmaceutical Research, 14(1):141-147.

Abstracts of the 1999 Joint Chubu and Kansai Branch Conference and Symposia of Japan Society for Bioscience, Biotechnology, and Agrochemistry, (1999) p. 48.

Acquaviva et al., "Targeting KRAS-Mutant Non-Small Cell Lung Cancer with the Hsp90 Inhibitor Ganetespib", Mol Cancer Ther, Dec. 2012, 11(12), pp. 2633-2643.

Adderly et al., 2019, KRA-mutant non-small cell lung cancer: converging small molecules and immune checkpoint inhibition, EBioMedicine, 41:711-716.

Agarwal et al., "OP449, a Novel SET Antagonist, Is Cytotoxic to Leukemia Cells and Enhances Efficacy of Tyrosine Kinase Inhibitors in Drug-Resistant Myeloid Leukemias," pursuant to an EMBASE record for a Conference ABSTRACT: 603. Oncogenes and Tumor Suppressors: Poster II (Nov. 15, 2013) Blood (2013) 122(21): 2511.

Aggarwal et al., Antiangiogenic agents in the management of non-small cell lung cancer: Where do we stand now and where are we headed? Cancer Biology & Therapy (2012), 13(5), 247-263.

Ahmed et al. "A new rapid and simple non-radioactive assay to monitor and determine the proliferation of lymphocytes: an alternative to [$^3$H]thymidine incorporation assay." J. Immunol. Methods. 170, 211-224 (1994).

Akerlund et al., "Diketopiperazine-Based Polymers from Common Amino Acids," Journal of Applied Polymer Science, (2000) 78 (12), 2213-2218.

Algaier et al. "The effects of dimethyl sulfoxide on the kinetics of tubulin assembly." Biochim. Biophys. Acta. 954, 235-43 (1988).

Ali et al. "Toxicity of echinulin from Aspergillus chevalieri in rabbits." Toxicology Letters. (1989) 48: 235-41.

Asahina, T., "Spectrochemical Study of Amino-acid Anhydrides," Bulletin of the Chemical Society of Japan, (1930) 5, 354-365.

Augustin, M. "Die Umsetzung des 2,5-Diketopiperazins mit Aldehyden und Nitrosoverbindungen" Journal für Praktische Chemie, (1966) 32(4), 158-166.

Aviel-Ronen et al., "K-ras Mutations in Non-Small-Cell Lung Carcinoma: A Review," *Clinical Lung Cancer* (Jul. 2006) vol. 8, No. 1, pp. 30-38.

Bankowska et al., Derivatives of 1,2,3-triazole. Potential drugs?, Wiadomosci Chemiczne (2012), 66(11-12), 993-1022.

Beavis et al., "Dual PD-1 and CTLA-4 Checkpoint Blockade Promotes Antitumor Immune Responses through CD4$^+$Foxp$^3$—Cell-Mediated Modulation of CD103$^+$ Dendritic Cells," Cancer Immunol Res (Sep. 2018) 6(9):1069-1081.

Bergman et al., Ariloxy Substituted N-arylpiperazinones as Dual Inhibitors of Farnesyltransferase and Geranylgeranyltransferase-1, Bioorg & Med Chem Lttrs. (Mar. 2001) 11:1411-1415.

Bertelsen et al., "Vascular effects of plinabulin (NPI-2358) and the influence on tumour response when given alone or combined with radiation," International Journal of Radiation Biology (2011), 87(11), 1126-1134.

Bertino J., et al., "Principles of Cancer Therapy." Cecil Textbook of Medicine. Eds. Lee Goldman, et al. 21nd ed., (2000), Chapter 198, pp. 1060-1074.

Blayney et al., "Plinabulin, a Novel Small Molecule That Ameliorates Chemotherapy-Induced Neutropenia, Is Administered on the Same Day of Chemotherapy and Has Anticancer Efficacy", Meeting Info.: 58th Annual Meeting and Exposition of the American Society-of-Hematology (ASH), Blood (2016) 128(22): 2508.

Bond et al. "The Synthesis of Viridamine, a Penicillium Viridicatum Mycotoxin." Synthetic Commun. 19 (13&14), 2551-2566 (1989).

Borisy, G.G. "A Rapid Method for Quantitative Determination of Microtubule Protein using DEAE—Cellulose Filters." Anal. Biochem. 50, 373-385 (1972).

Braga et al. "Crystal Polymorphism and Multiple Crystal Forms," Struct Bond (2009) 132:25-50.

Brahmer et al., "Safety and Activity of Anti-PD-L1 Antibody in Patients with Advanced Cancer," N Engl J Med (2012) 366:2455-2465.

Burtles, Sally, "Transition from Preclinical to first-in-man Phase", Expert Scientific Group on Phase One Clinical Trials Final Report, Presentation Jun. 19, 2006, pp. 35-38.

Cai, Small molecule vascular disrupting agents: potential new drugs for cancer treatment, a 2009 update, Frontiers in Anti-Cancer Drug Discovery (2010), 1, 380-427.

Cai, Sui X., "Small Molecule Vascular Disrupting Agents: Potential New Drugs for Cancer Treatment", Recent Pat Anticancer Drug Discov. (2007) 2(1): 79-101.

Caira, 1998, Crystalline polymorphism of organic compounds, Topics in Current Chemistry, 198:163-208.

Callahan et al., "At the Bedside: CTLA-4- and PD-1-blocking antibodies in cancer immunotherapy", J Leukocyte Biol, vol. 94, Jul. 2013, pp. 41-53.

Carter et al., "No patient left behind: The promise of immune priming with epigenetic agents," Oncoimmunology (2017) vol. 6, No. 10, e1315486 (13 pages).

Chaplin et al., "Antivascular approaches to solid tumour thereapy: evaluation of tubulin binding agents", Br. J. Cancer 1996, 74 (Suppl. XXVII), S86-S88.

Chen et al., "Adjuvant effect of docetaxel on the immune responses to influenza A H1N1 vaccine in mice," BMC Immunology (2012) 13:36, pp. 1-12.

(56) References Cited

OTHER PUBLICATIONS

Chin et al., "Immune Intervention with Monoclonal Antibodies Targeting CD152 (CTLA-4) for Autoimmune and Malignant Diseases," Chang Gung Med J (Jan.-Feb. 2008) vol. 31, No. 1, pp. 1-15.
ClinicalTrials.gov Identifier NCT00892931, "Phase 2 study MPC-6827 for recurrent glioblastoma multiforme," (Oct. 14, 2011). [retrieved from internet on Jul. 30, 2019] <URL: https://clinicaltriais.gov/ct2/show/NCT00892931> 7 pages.
ClinicalTrials.gov Identifier NCT02846792, "Nivolumab and Plinabulin in Treating Patients With Stage IIIB-IV, Recurrent, or Metastatic Non-small Cell Lung Cancer," (Jul. 27, 2016). [retrieved from internet on Sep. 17, 2019], <URL: https://clinicaltrials.gov/ct2/show/NCT02846792?term=plinabuilin&rank=1> 11 pages.
Cole, P., "Durvalumab, Human anti-PD-L1 monoclonal antibody Immune checkpoint inhibitor Oncolytic", Drugs of the Future 2014, 39(12): pp. 843-847.
Cooper et al., "Response to BRAF Inhibition in Melanoma Is Enhanced When Combined with Immune Checkpoint Blockade," Published OnlineFirst Apr. 29, 2014; DOI: 10.1158/2326-6066.CIR-13-0215; Cancer Immunol Res (Jul. 2014) 2(7) 643-654.
Costa et al., "Analyses of selected safety endpoints in phase 1 and late-phase clinical trials of anti-PD-1 and PD-L1 inhibitors: prediction of immune-related toxicities," Oncotarget (2017) vol. 8, No. 40, pp. 67782-67789.
Cui et al. "Novel Mammalian Cell Cycle Inhibitors, Tryprostatins A, B and Other Diketopiperazines Produced by Aspergillus fumigatus." J. Antibiotics. 49(6), 534-40 (1996).
Cui et al. "Novel Mammalian Cell Cycle Inhibitors, Tryprostatins A, B and Other Diketopiperazines Produced by Aspergillus fumigatus." J. Antibiotics. 49(6): 527-33 (1996).
Davis et al., ZD6126: A Novel Vascular-targeting Agent That Causes Selective Destruction of Tumor Vasculature, Cancer Research (Dec. 15, 2002) 62: 7247-7253.
Dörwald, F., "Side Reactions in Organic Synthesis" Wiley-VCH Verlag GmbH & Co. KgaA, Weinheim, (2005), book cover and preface p. IX only.
Drug Approval and Licensing Procedures in Japan 2001, 2001, pp. 243-244.
Dunitz et al., "Disappearing Polymorphs," Acc. Chem. Res. (1995) vol. 28, No. 4, pp. 193-200.
Fernandez-Medarde et al., Mar. 2011, Ras in cancer and developmental diseases, Genes & Cancer, 2(3): 344-358.
Ferrer et al., Plinabulin: tubulin polymerization inhibitor vascular-disrupting agent oncolytic, Drugs of the Future (2010), 35(1), 11-15.
Folkes et al., Synthesis and In Vitro Evaluation of a Series of Diketopiperazine Inhibitors of Plasminogen Activator Inhibitor-1, Bioorg & Med Chem Lttrs., (Jul. 2001) 11: 2589-2592.
Frost et al., Novel Syngeneic Pseudo-orthotopic Prostate Cancer Model: Vascular, Mitotic and Apoptotic Responses to Castration, Microvasc Research (Dec. 2004) 69: 1-9.
Fukushima et al., "Biological Activities of Albonoursin," J. Antibiotics, (1973) 26:175.
Funato et al., 2000, Anti-K-ras rybozyme induced growth inhibition and increased chemosensitivity in human colon cancer cells, Gene Cancer Therapy, 7(3):495-500.
Gallina et al., "Condensation of 1,4-diacetylpiperazine-2,5-dione with aldehydes", Tetrahedron 1974, 30, 667-673.
Gameiro et al., "Exploitation of differential homeostatic proliferation of T-cell subsets following chemotherapy to enhance the efficacy of vaccine-mediated antitumor responses," Cancer Immunology Immunotherapy (2011) vol. 60, No. 9, pp. 1227-1242.
Garris et al., "Successful Anti-PD-1 Cancer Immunotherapy Requires T Cell-Dendritic Cell Crosstalk Involving the Cytokines IFN-( and IL-12," Immunity (Dec. 18, 2018) 49, pp. 1-14, e1-e7 (22 pages).
Goldani et al. "Treatment of murine pulmonary mucormycosis with SCH 42427, a broad-spectrum triazole antifungal drug", Correspondence, J Antimicrob Chemother. 33, 369-372 (1994).
Goldfarb et al., "Synthesis of β-2-thienylalanine," Izvestiya Akademii Nauk SSSR, Seriya Khimicheskaya, (1958) 98-100, as abstracted by CAPLUS.

Gordon et al. "Reductive Alkylation on a Solid Phase: Synthesis of a Piperazinedione Combinatorial Library." J. Bioorg. Med. Chem. Letters. 5, 47-50 (1995).
Granville et al., Release of Cytochrome c1 Bax Migration, Bid Cleavage, and Activation of Caspases 2, 3, 6, 7, 8, and 9 during Endothelial Cell Apoptosis, Am J Path., (Oct. 1999) 155(4): 1021-1025.
Gridelli et al., Vascular disrupting agents: a novel mechanism of action in the battle against non-small cell lung cancer, Oncologist (2009), 14(6), 612-620.
Gu et al., "Identification of CTLA-4 isoforms produced by alternative splicing and their association with myasthenia gravis," Clinical Immunology (Sep. 2008) vol. 128, Issue 3, pp. 374-381.
Gura, Trisha, "Cancer Models: Systems for Identifying New Drugs are Often Faulty", Science 7(Nov. 1997) 278(5340): 1041-1042.
Hamel, E. "Antimitotic Natural Products and Their Interactions with Tubulin." Med. Res. Rev. (1996) 16(2): 207-31.
Hartwell et al. "Checkpoints: Controls that Ensure the Order of Cell Cycle Events." Science. 246, 629-34 (1989).
Hayakawa, Structure-activity relationship analysis, Japnaese Journal of Cancer and Chemotherapy, (2004), 31(4):526-528.
Hayashi et al., "Total Synthesis of Anti-microtubule Diketopiperazine Derivatives: Phenylahistin and Aurantiamine," J. Org. Chem., (2000) 65: 8402-8405.
Hayashi et al., Medicinal chemistry and chemical biology of diketopiperazine-type antimicrotubule and vascular-disrupting agents, Chemical & Pharmaceutical Bulletin (2013), 61(9), 889-901.
Hayashi et al., Small peptide-based medicinal chemistry for intractable disease, Peptide Science (2009), vol. Date 2008, 45th, 139-140.
He et al., "Low-dose paclitaxel enhances the anti-tumor efficacy of GM-CSF surface-modified whole-tumor-cell vaccine in mouse model of prostate cancer," Cancer Immunology Immunotherapy (2011) vol. 60, No. 5, pp. 715-730. Abstract.
Heist et al., "Abstract C30: Phase 1/2 study of the vascular disrupting agent (VCA) plinabulin (NPI-2358) combined with docetaxel in patients with non-small cell lung cancer (NSCLC)," *Mol. Cancer Ther.*, 2009; 8(12 Suppl):C30, 2 pages.
Heist et al., "Randomized Phase 2 Trial of Plinabulin (NPI-2358) Plus Docetaxel in Patients with Advanced Non-Small Lung Cancer (NSCLC)," 2014 ASCO Annual Meeting. . (abstr 8054) Poster Presentation. Retrieved from the internet Jul. 17, 2017: <http://meetinglibrary.asco.org/record/92548/poster>.
Heist et al., "Randomized phase 2 trial of plinabulin (NPI-2358) plus docetaxel in patients with advanced non-small cell lung cancer (NSCLC)." J. Clin. Oncol. (2014) vol. 32, No. 5s, (suppl; abstr 8054).
Helleman et al. "The International Journal of Biochemistry & Cell Biology," vol. 42, pp. 25-30 (2010).
Horak et al. "Structures of the Austalides A-E, Five Novel Toxic Metabolites from Aspergillus ustus." J Chem Soc Chem Commun. (1981) 1265-67.
http://scienceandresearch.homeoffice.gov.uk/animal-research/publications-and-reference/001-abstracts/abstracts2-2006/02november-2006/457?view=Html; "Abstract #457, Animals in Scientific Procedures (2006)"; (accessed on Nov. 19, 2008).
Hursthouse et al., "Why Do Organic Compounds Crystallise Well or Badly or Ever so Slowly? Why Is Crystallisation Nevertheless Such a Good Purification Technique?," Organic Process Res & Devel (2009) vol. 13, No. 6, pp. 1231-1240.
Hyun et al., "Valine dehydrogenase from Streptomyces albus: gene cloning, heterologous expression and identification of active site by site-directed mutagenesis," FEMS Microbiology Letters (Jan. 1, 2000) 182: 29-34.
Iwasaki, S. "Antimitotic Agents: Chemistry and Recognition of Tubulin Molecule." Med Res Rev. (1993) 13: 183-198.
Iwasaki, S. "Bioactive Natural Products Interfering with Microtubule Function." Kagaku to Seibutsu. 32(3): 153-159 (1994).
Ji et al., Tubulin Colchicine Binding Site Inhibitors as Vascular Disrupting Agents in Clinical Developments, Current Medicinal Chemistry (2015), 22(11), 1348-1360.

(56) References Cited

OTHER PUBLICATIONS

Jiang et al., "A Novel Peptide Isolated from a Phage Display Peptide Library with Trastuzumab Can Mimic Antigen Epitope of HER-2*," (Feb. 11, 2005) J Biol Chem, vol. 280, No. 6, pp. 4656-4662.
Johnson et al. "Kinetic Analysis of Microtubule Self-assembly in Vitro." J. Mol. Biol. 117, 1-31 (1977).
Jure-Kunkel M. et al., "Synergy between chemotherapeutic agents and CTLA-4 blockade in preclinical tumor models", Cancer Immunol. Immunother. 2013, vol. 62, pp. 1533-1545.
Kakoulidou et al., "Human Soluble CD80 is Generated by Alternative Splicing, and Recombinant Soluble CD80 Binds to CD28 and CD152 Influencing T-cell Activation," Scandinavian J. Immunol (Nov. 2007) 66(5):529-537.
Kamb, Alexander, "What's wrong with our cancer models?", Nature Reviews Drug Discovery (Feb. 2005) 4: 161-165.
Kanoh et al., "(−)—Phenylahistin: A New Mammalian Cell Cycle Inhibitor Produced by Aspergillus USTUS," Bioorganic & Medicinal Chemistry Letters, (1997) 7: 2847-2852.
Kanoh et al., "(−)—Phenylahistin Arrests Cells in Mitosis by Inhibiting Tubulin Polymerization," The Journal of Antibiotics, (1999) 52: 134-141.
Kanoh et al., "Antitumor Activity of Phenylahistin in Vitro and in Vivo," Bioscience Biotechnology Biochemistry, (1999) 63(6): 1130-1133.
Kanoh et al., "Synthesis and Biological Activities of Phenylahistin Derivatives," Bioorganic & Medicinal Chemistry, (1999) 7: 1451-1457.
Kanthou et al., Microtubule depolymerizing vascular disrupting agents: novel therapeutic agents for oncology and other pathologies, International Journal of Experimental Pathology(2009), 90(3), 284-294.
Kanzaki et al., A Novel Potent Cell Cycle Inhibitor Dehydrophenylahistin-Enzymatic Synthesis and Inhibitory Activity toward Sea Urchin Embryo, The Journal of Antibiotics, (Dec. 2002) 55(12): 1042-1047.
Kanzaki et al., "Effective Production of Dehydro Cyclic Dipeptide Albonoursin Exhibiting Pronudear Fusion Inhibitory Activity, I. Taxonomy and Fermentation," The Journal of Antibiotics, (1999) 52: 1017-1022.
Kanzaki et al., "Effective Production of Dehydro Cyclic Dipeptide Albonoursin Exhibiting Pronudear Fusion Inhibitory Activity, II. Biosynthetic and Bioconversion Studies," The Journal of Antibiotics, (2000) 53(1): 58-62.
Kanzaki et al., "Enzymatic dehydrogenation of cyclo(L-Phe-L-Leu) to a bioactive derivative, albonoursin," Journal of Molecular Catalysis B: Enzymatic (1999) 6(3): 265-270.
Kanzaki et al., "Enzymatic Synthesis of Physiologically Active Substances Utilizing a Novel System for the Synthesis of Diketopiperazines Comprising Dehydroamino Acids as Constituents," Abstracts of Papers Presented at the 1999 Meeting of the Society for Actinomycetes Japan, (1999) 42 (Abstract Only).
Kanzaki et al., "Novel Cyclic Dipeptide Dehydrogenase and Assay Method for Its Activity," Scientific Reports of the Faculty of Agriculture, Okayama University, (1999) 88: 7-11.
Kashyap et al., Sep. 24, 2019, GEF-H1 signaling upon microtubule destabilization is required for dindritic cell activation and specific anti-tumor responses, Cell Reports, 28:3367-3380.
Keepers et al. "Comparison of the Sulforhodamine B Protein and Tetrazolium (MTT) Assays for in vitro Chemosensitivity Testing." Eur. J. Cancer. 27, 897-900 (1991).
Kharbanda et al., 2014, MUC1-C confers EMT and KRAS independence in mutant KRAS lung cancer cells, Oncotarget, 5(19):8893-8905.
Kim et al. "Polymer attached cyclic peptides, tetrahedron: Asymmetry." 3(11): 1421-1430 (1992).
Kingston, Correction to Tubulin-interactive natural products as anticancer agents, Journal of Natural Products (2011), 74(5), 1352.
Kingston, Tubulin-Interactive Natural Products as Anticancer Agents, Journal of Natural Products (2009), 72(3), 507-515.
Kobayashi et al., "Microtubule Assembly Regulators of Microbial Origin," Abstract of Paper Read at the 1989 Symposium on the Chemistry of Natural Products, (1989) 51.
Kola et al., "Can the pharmaceutical industry reduce attrition rates?", Nature Reviews Drug Discovery (2004) 3:711-715.
Kondoh et al. "Effects of Tryprostatin Derivatives on Microtubule Assembly In Viro and In Situ." J. Antibiotics. 51, 801-04 (1998).
Kopple et al., "A Convenient Synthesis of 2,5-Piperazinediones1a," The Journal of Organic Chemistry, (1967) 33: 862-864.
Kreamer K., "Immune checkpoint blockade: A New Paradigm in Treating Advanced Cancer", J. Adv. Pract. Oncol., 2014, vol. 5, pp. 418-431.
Krishan, A. "Rapid Flow Cytofluorometric Analysis of Mammalian Cell Cycle by Propidium Iodide Staining." J. Cell Biol. 66, 188-193 (1975).
Kupchan et al. "Steganacin and Steganangin, Novel Antileukemic Lignan Lactones from Steganotaenia araliacea 1-3." J. Am. Chem. Soc. (1973) 95(4): 1335-36.
Küster & Koeppenhöfer, "Über eininge Pyrrolderivate," Z. Physiol, Chem., (1927) 172:126-137.
Lacey et al. "Interaction of Phomopsin A and Related Compounds with Purified Sheep Brain Tubulin." Biochem. Pharmacol. 36, 2133-38 (1987).
Laemmli, U.K. "Cleavage of Structural Proteins during the Assembly of the Head of Bacteriophage T4." Nature. 227, 680-85 (1970).
Larsen et al. "Aurantiamine, A Kiketopiperazine from Two Varieties of Penicillium Aurantiogriseum." Phytochemistry. 31, 1613-1615 (1992).
Leaf, Clifton, "Why are we losing the war on cancer (And how to win it)?", Health Administrator (2005) XVII(1): 172-183.
Lee et al. "The Reconstitution of Microtubules from Purified Calf Brain Tubulin." Biochemistr. 14(23), 5183-87 (1975).
Lee et al., "A practical guide to pharmaceutical polymorph screening & selection," Asian Journal of Pharmaceutical Sciences (2014) vol. 9, pp. 163-175.
Lee et al., Colchicine site inhibitors of microtubule integrity as vascular disrupting agents, Drug Development Research (2008), 69(6), 352-358.
Li, Y., et al. "Interaction of marine toxin dolastatin 10 with porcine brain tubulin: competitive inhibition of rhizoxin and phomopsin A binding." Chem. Biol. Interact. 93, 175-83 (1994).
Liao et al., "Design and synthesis of novel soluble 2,5-diketopiperazine derivatives as potential anticancer agents,"European J Med Chem (2014) 83:236-244.
Liou et al., Aug. 12, 2004, Concise synthesis and structure-activity relationships of combretastatin A-4 analogues, 1-aroylindoles and 3-aroylindoles, as novel classes of potent antitubulin agents, Journal of Medicial Chemstry, 47(17):4247-4257.
Liu et al., "The BRAF and MEK Inhibitors Dabrafenib and Trametinib: Effects on Immune Function and in Combination with Immunomodulatory Antibodies Targeting PD-1, PD-L1, and CTLA-4," Clin Cancer Res (2015) 21(7) 1639-1651.
Liwo et al. "Origin of the Ring-Ring Interaction in Cyclic Dipeptides Incorporating an Aromatic Amino Acid." Tetrahedron Lett. 26, 1873-1876 (1985).
Lloyd et al., Abstract A07: Plinabulin: Evidence for an immune-mediated mechanism of action, In: Proceedings of the AACR Special Conference: Function of Tumor Microenvironment in Cancer Progression; Jan. 7-10, 2016; San Diego, CA. Philadelphia (PA): AACR; Cancer Research. Aug. 2016. 76(15 Supp.): abstract nr A07.
Lu et al., Nov. 2012, An overview of tubulin inhibitors that interact with the colchicine binding site, Pharmaceutical Research, 29(11):2943-2971.
Luduena, R.F. "Contrasting Roles of Tau and Microtubule-associated Protein 2 in the Vinblastine-induced Aggregation of Brain Tubulin." J. Biol. Chem. 259:12890-98 (1984).
Lyman et al., "Risk Models for Predicting Chemotherapy-Induced Neutropenia," The Oncologist (2005) 10:427-437.
Lynch et al., "Ipilimumab in Combination With Paclitaxel and Carboplatin as First-Line Treatment in Stage IIIB/IV Non-Small-Cell Lung Cancer: Results From a Randomized, Double-Blind, Multicenter Phase II Study," (Jun. 10, 2012) J Clin Oncol, vol. 30, No. 17, pp. 2046-2054.

(56) References Cited

OTHER PUBLICATIONS

Mahindroo et al., "Antitubulin Agents for the Treatment of Cancer—A Medicinal Chemistry Update", Expert Opin. Ther. Patents (2006) 16(5): 647-691.
Mahoney et al., "The Next Immune-Checkpoint Inhibitors: PD-1/PD-L1 Blockade in Melanoma," Clinical Therapeutics (Apr. 2015) vol. 37, Issue 4, pp. 764-782. Abstract.
Matsuda et al., "Pilot study of WT1 peptide-pulsed dendritic cell vaccination with docetaxel in esophageal cancer," Oncology Letters (Jul. 2018) vol. 16, No. 1, pp. 1348-1356.
Millward et al., "Phase I trial of NPI-2358 (a novel vascular disrupting agent) plus docetaxel," J. Clin. Oncol. (May 2009) 27(15S): 3571-3571, Abstract.
Millward et al., "Phase 1 study of the novel vascular disrupting agent plinabulin (NPI-2358) and docetaxel," The Journal of New Anticancer Agents, vol. 3, No. 30, Feb. 16, 2011 plinabulin (NPI-2358) and docetaxel, Investigational New Drugs (2011), 30(3), 1065-1073.
Mita et al., "Phase 1 First-in-Human Trial of the Vascular Disrupting Agent Plinabulin (NPI-2358) in Patients with Solid Tumors or Lymphomas," *Clinical Cancer Research* (2010), 16(23), 5892-5899.
Mita et al., "Phase II study of docetaxel with or without plinabulin (NPI-2358) in patients with non-small cell lung cancer (NSCLC)", *J. Clin. Oncol.*, 2010, vol. 28, No. 15 supplement. Abstract 7592, 2 pages.
Mita et al., Randomized Phase 2 Study of Docetaxel +/− Plinabulin (NPI-2358) in Patients with Non-Small Cell Lung Cancer (NSCLC), *Poster Presentation at ACS Annual '10 Meeting* (Jun. 4-8, 2010) 1 page.
Mitsudomi et al., "Mutations of ras genes distinguish a subset of non-small-cell lung cancer cell lines from small-cell lung cancer cell lines," *Oncogene* (Aug. 1991) vol. 6, No. 8, pp. 1352-1362.
Mohanlal et al., "The plinabulin/docetaxel combination to mitigate the known safety concerns of docetaxel," J Clin Oncol (2016) 34(15_suppl), Abstract e20595.
Muguruma et al., OP-20: "Application of Fc-selective Z33-peptide to the preparation of non-covalent-type antibody-antimocrotubule plinabulin conjugate," 34th European Peptide Symposium 2016 & 8th International Peptide Symposium, Journal of Peptide Sci (Sep. 5, 2016—5:30pm) 22 Supplement 2 ISSN: 1099-1387 in English (Oral Presentation). Abstract.
Nagaria et al., "Flavopiridol Synergizes with Sorafenib to Induce Cytotoxicity and Potentiate Antitumorigenic Activity in EGFR/HER02 and Mutant RAS/RAF Breast Cancer Model Systems," NEOPLASIA (Aug. 2013) vol. 15, No. 8, pp. 939-951.
Neidle, Stephen, ed., Cancer Drug Design and Discovery , 9th Edition, Elsevier/Academic Press, (2008) Chapter 18, pp. 427-431.
Nema et al., Excipients and Their Role in Approved Injectable Products: Current Usage and Future Directions, PDA J Pharm Sci and Tech 2011, 65 287-332.
Neuteboom et al., "450 Poster NPI-2358, a novel tumor vascular disrupting agent potentiates the anti-tumor activity of docetaxel in the non small cell lung cancer model MV522," EJC Supplements (2008) 6(12):141.
Nicholson et al., NPI-2358 is a tubulin-depolymerizing agent: in-vitro evidence for activity as a tumor vascular-disrupting agent, Anti-Cancer Drugs (2005), vol. Date 2006, 17(1), 25-31.
Niemann et al., "The Synthesis of the Three Isomeric dl-β-Pyridylalanines" Journal of the American Chemical Society, (1942) 64(7): 1678-1682.
Nihei et al., "Evaluation of antivascular and antimitotic effects of tubulin binding agents in solid tumor therapy", Jpn. J. Cancer. Res. 1999, 90, 1387-1395.
Nitecki et al., "A Simple Route to Sterically Pure Diketopiperazines1," The Journal of Organic Chemistry, (1968) 33:864-866.
Ohaegbulam et al., "Human cancer immunotherapy with antibodies to the PD-1 and PD-L1 pathway," Trends Mol Med, (Oct. 30, 2014) 21(1): pp. 24-33.

Ott et al., "CTLA-4 and PD-1/PD-L1 Blockade: New Immunotherapeutic Modalities with Durable Clinical Benefit in Melanoma Patients," Clin Cancer Res (Oct. 1, 2013) 19(19): pp. 5300-5309.
Paik et al., "A Phase 2 Study of Weekly Albumin-Bound Paclitaxel (Abraxane®) Given as a Two-Hour Infusion", Cancer Chemother. Pharmacol., Nov. 2011, vol. 68, No. 5, pp. 1331-1337.
Paolo et al., Jun. 2013, Selumetinib in advanced non small cell lung cancer (NSCLC) harbouring KRAS mutation: endless clinical challenge to KRAS-mutant NSCLC, Rev. Recent Clin Trials, 8(2):93-100 (abstract).
Pardoll et al., "The blockade of immune checkpoints in cancer immunotherapy," Nat Rev Cancer (May 4, 2016) 12(4): 252-264.
Pattingre et al., "Amino Acids Interfere with the ERK1/2-dependent Control of Macroautophagy by Controlling the Activation of Raf-1 in Human Colon Cancer HT-29 Cells," J Biol Chem (May 9, 2003) vol. 278, No. 19, pp. 16667-16674.
Perez, Edith A., "Paclitaxel in Breast Cancer," *The Oncologist*, 1998, vol. 3, pp. 373-389.
Petrillo et al., Novel VEGF-independent strategies targeting tumor vasculature: clinical aspects, Current Pharmaceutical Design (2012), 18(19), 2702-2712.
Pettit et al. "Antineoplastic Agents. 291. Isolation and Synthesis of Combretastatins A-4, A-5, and A-6 1a." J. Med. Chem. (1995) 38: 1666-1672.
Prior et al., "A Comprehensive Survey of Ras Mutations in Cancer" *Cancer Res*. (2012) vol. 72, No. 10, pp. 2457-2467.
Raza et al., 2014, Polymorphism: the phenomenon affecting the performance of drugs, SOJ Pharmacy & Pharmaceutical Sciences, 10 pp.
Reck, M., "What future opportunities may immuno-oncology provide for improving the treatment of patients with lung cancer?" (2012) Annals of Oncology (Sep. 2012) 23 (Supp. 8) viii28-viii34.
Remington, "The Science and Practice of Pharmacy, 20th Ed" (2000) p. 709.
Rhodes, John, "Section Review: Biologicals & Immunologicals: Therapeutic potential of Schiff base-forming drugs," Expert Opinion on Investigational Drugs (1996) vol. 5, Issue 3, pp. 257-268.
Riemer et al., "Matching of trastuzumab (Herceptin®) epitope mimics onto the surface of Her-2/neu—a new method of epitope definition," Mol Immunol 42 (2005) pp. 1121-1124.
Roberge et al., "Antitumor Drug Fostriecin Inhibits the Mitotic Entry Checkpoint and Protein Phosphatases 1 and 2A." Cancer Res. 54, 6115-21 (1994).
Roberts et al, "Trends in the Risks and Benefits to Patients with Cancer Participating in Phase 12 Clinical Trials", JAMA (2004) 292(17): 2130-2140.
Rowinsky et al, "The clinical pharmacology and use of antimicrotubule agents in cancer chemotherapeutics", Pharmacol. Ther. 1991, 52, 35-84.
Rowinsky et al. "Taxol: A Novel Investigational Antimicrotubule Agent." J. Natl. Cancer Inst. 82(15): 1247-59 (1990).
Rozali et al., "Programmed Death Ligand 2 in Cancer-Induced Immune Suppression," Clinical and Developmental Immunology (2012) Article ID 656340, pp. 1-8.
Sackett, D.L. "Podophyllotoxin, Steganacin and Combretastatin: Natural Products that Bind at the Colchicine Site of Tubulin." Pharmacol. Ther. (1993) 59:163-228.
Saito et al., "Synthesis of novel octahydro-1, 5-imino-3-benzazocin-4, 7, 10-trione derivatives having a methyl group at the C-2 position as ABC ring models of saframycins," Chemical & Pharmaceutical Bulletin (1997) 45(7):1120-1129.
Scholl et al., "Synthetic Lethal Interaction between Oncogenic KRAS Dependency and the STK33 Suppression in Human Cancer Cells", Cell (May 29, 2009) 137 pp. 821-834.
Sele et al., Jul. 2016, Novel 4-(pyrimidin-2-yl)morpholines targeting the colchicine-binding site of tubuline, Cancer Research, 76(14):abstract.
Sezaki et al., "Drug Delivery Systems", Drug Development, (Jul. 1989) 13: 116, Table 2. 29.

(56) References Cited

OTHER PUBLICATIONS

Shen et al., NPI-2358 rapidly inhibit blood flow in tumor treatment by analyzing dynamic contrast enhanced magnetic resonance imaging parameters, Zhonghua Zhongliu Fangzhi Zazhi (2010), 17(7),488-490, 494.

Shen et al., Time- and dose-dependent vascular changes induced by the novel vascular disrupting drug NPI-2358 in a murine cancer model monitored with DCE-MRI, U.S. Chinese Journal of Lymphology and Oncology(2010), 9(4), 151-153.

Sherline et al. "Binding of Colchicine to Purifiied Microtubule Protein." J. Biol. Chem. 250, 5481-86 (1975).

Shi, Q et al, "Recent progress in the development of tubulin inhibitors as antimitotic antitumor agents", Curr. Pharm. Des. 1998, 4, 219-248.

Singh et al., "A novel vascular disrupting agent plinabulin triggers JNK-mediated apoptosis and inhibits angiogenesis in multiple myeloma cells," Blood (2011), 117(21), 5692-5700.

Siwicka et al., "Diastereodivergent Synthesis of 2,5-diketopiperazine Derivatives of Beta-Carboline and Isoquinoline from L-amino Acids," Tetrahedron: Asymmetry (Mar. 7, 2005) 16(5): 975-993.

Smedsgaard et al. "Using direct electrospray mass spectrometry in taxonomy and secondary metabolite profiling of crude fungal extracts." J. Microbiol. Meth. (1996) 25: 5-17.

Sölter et al., Barettin, Revisited? Tetrahed Lttrs. (Mar. 2002) 43: 3385-3386.

Spear et al., Vascular disrupting agents (VDA) in oncology: advancing towards new therapeutic paradigms in the clinic, Current Drug Targets (2011), 12(14), 2009-2015.

Stein, J., ed. "Internal Medicine," Fourth Edition, Mosby-Year Book, Inc., (1994), Chapters 71-72, pp. 699-729.

Stenehjem et al., "PDl/PDLI inhibitors for the treatment of advanced urothelial bladder cancer," OncoTargets and Therapy (2018) 11:5973-5989.

Steyn, P.S. "The Structures of Five Diketopiperazines from Aspergillus Ustus." Tetrahedron. 29, 107-120 (1973).

Sugar et al. "Comparison of Three Methods of Antifungal Susceptibility Testing with the Proposed NCCLS Standard Broth Macrodilution Assay: Lack of Effect of Phenol Red." Diagn Micro and Infect Diseases. 21, 129-133 (1995).

Takahashi et al. "Rhizoxin binding to tubulin at the maytansine-binding site." Biochem. Biophys. Acta. 926, 215-23 (1987).

Talmadge et al., Murine models to evaluate novel and conventional therapeutic strategies for cancer., Am J Pathol, 2007, vol. 170, Issue 3, pp. 793-804.

Thorpe, Philip E., "Vascular Targeting Agents as Cancer Therapeutics," Clinical Cancer Research, vol. 10, 415-427, Jan. 15, 2004.

Tiwari et al. "A pH- and Temperature-Dependent Cycling Method that doubles the Yield of Microtubule Protein." Anal. Biochem. 215, 96-103 (1993).

Tonra et al., "Predictive models for tumour cell targeting with plinabulin, derived from in vitro screening and Affymetrix mRNA expression data," Proc Am Assoc Cancer Res (2019) vol. 60, p. 321, Abstract #1254.

Topalian et al., "Safety, Activity, and Immune Correlates of Anti-PD-1 Antibody in Cancer," N Engl J Med. (Jun. 28, 2012) 366(26):2443-2454.

Tozer et al., Tumour vascular disrupting agents: combating treatment Resistance, British Journal of Radiology (2008), 81(Spec. Iss. 1), S12-S20.

Turner et al. "Recent Advances in the Medicinal Chemistry of Antifungal Agents." Current Pharmaceutical Design. 2, 209-224 (1996).

US Food and Drug Administration, Highlights of prescribing information, retrieved Apr. 16, 2020 from https://www.accessdata.fda.gov/drugsatfda_docs/label/2015/125031s180lbl.pdf, Rev. Nov. 2015, Reference ID:4192944.

Usui et al. "Tryprostatin A, a specific and novel inhibitor of microtubule assembly." Biochem J. 333, 543-48 (1998).

Van der Waerden, B.L., "Wirksamkeits- und Konzentrationsbestimmung durch Tierversuche." Arch Exp Pathol Pharmakol. 195, 389-412, (1940).

Verdier-Pinard et al., "Structure-Activity Analysis of the Interaction of Curacin A, the Potent Colchicine Site Antimitotic Agent, with Tubulin and Effects of Analogs on the Growth of MCF-7 breast Cancer Cells." Mol. Pharmacol., 53, 62-76 (1998).

Voskoglou-Nomikos et al., Clinical predictive value of the in vitro cell line, human xenograft, and mouse allograft preclinical cancer models, National Cancer Institute of Canada Clinical Trials Group et al., 2003, vol. 9, pp. 4227-4239.

Wang, T. et al. 1998 "Microtubule interfering agents activate c-Jun N-terminal kinase/stress-activated protein kinase through both Ras and apoptosis signal-regulating kinase pathways". J Biol Chem. vol. 273, No. 9, pp. 4928-4936.

Wang, Y. et al., "Structures of a diverse set of colchicine binding site inhibitors in complex with tubulin provide a rationale fordrug discovery." FEBS Journal (2016) 283, 102-111.

Waters et al., Sep. 2018, KRAS: the critical driver and therapeutic target for pancreatic cancer, Cold spring Harb Perspect Med, 8(9), 23 pp.

Weisenberg et al. "The Colchicine-Binding Protein of Mammalian Brain and its Relation to Microtubules." Biochemistry (1968) 7(12): 4466-79.

Westcott et al., 2013, The genetics and biology of KRAS in lung cancer, Chinee Journal of Cancer, 32(2):63-70.

Wilt et al. "Anal cancer in Alaska; a retrospective study of incidence, treatment, and outcomes". Alaska Med Jul.-Sep. 2002; 44(3):56-9, 62.

Yahara et al. "Microtubule Organization of Lymphocytes and its Modulation by Patch and Cap Formation." Cell. 15, 251-259 (1978).

Yamato et al., "Clinical importance of B7-H3 expression in human pancreatic cancer," British Journal of Cancer (Oct. 20, 2009) 101, pp. 1709-1716.

Yamazaki et al. "Crystal Structure and Absolute Configuration of Fumitremorgin B, a Tremorgenic Toxin from Aspergillus Fumigatus Fres." Tetrahedron Lett. 1, 27-28 (1975).

Yamazaki et al. "Synthesis and Structure-Activity Relationship Study of Antimicrotubule Agents Phenylahistin Derivatives and a Didehydropiperazine-2,5-dione Structure", Journal of Medicinal Chemistry, 2012, vol. 55, No. 3, pp. 1056-1071.

Yamazaki et al., Drug discovery study on cyclic dipeptides anticancer drugs and chemical biological development, Idenshi Igaku Mook (2012), 21(Saishin Pepuchido Gosei Gijutsu to Sono Soyaku Kenkyu eno Oyo), 260-266.

Yamori T., "A Human Cell Line Panel for Screening Anti-Cancer Drugs", Jap. J. Cancer Chemother. 24, 129-35 (1997).

Yang et al., "The KRAS Mutation is Highly Correlated With EGFR Alterations in Patients With Non-small Cell Lung Cancer," Fooyin J Health Sci (2009) vol. 1(2): pp. 65-71.

Yeh et al., "A Phase 1 Trial Combining Plinabulin and Nivolumab for Metastatic Squamous NSCLC," International Association for the Study of Lung Cancer, Journal of Thoracic Oncology (Sep. 6, 2015) Abstract 602, p. 2.01-087.

Yin et al., "Human Mutations That Confer Paclitaxel Resistance," Mol. Cancer Ther. vol. 9(2), pp. 327-335 (2010).

Yokio et al., "Neihumicin. A New Cytotoxic Antibiotic From Micromonospora Neihuensis," The Journal of Antibiotics, (Apr. 1988) 41(4):494-501.

Yoshida, M.M. Protein Nucleic Acid Enzymes. 38, 1753-1765 (1993).

Yoshimatsu et al. "Mechanism of Action of E7010, an Orally Active Sulfonamide Antitumor Agent: Inhibition of Mitosis by Binding to the Colchicine Site of Tubulin." Cancer Res. 57, 3208-13 (1997).

Younis et al., 2011, The cost-utility of adjuvant chemotherapy using docetaxel and cylophosphamide compared with doxorubicin and cyclophosphamide in breast cancer, Current Oncology 18(8):e298-3296.

Zawadzka et al., "Diastereoselective Synthesis of 1-Benzyltetrahydroisoquinoline Derivatives from Amino Acids by 1,4 Chirality Transfer", Euro J Org Chem., (Jul. 2003) 2003(13): 2443-2453.

(56) References Cited

OTHER PUBLICATIONS

Zheng, Lei, "Does vaccine-primed pancreatic cancer offer better candidates for immune-based therapies?" Immunotherapy (2014) 6(10): 1017-1020.
Zou et al., Effect of Interleukin-1 Blockers, CK112, and CK116 on Rat Experimental Choroidal Neovascularization In Vivo and Endothelial Cell Cultures In Vitro, J Ocul Pharma Thera., (2006) 22(1): 19-25.
International ISR/WO dated Mar. 8, 2019 for PCT/US2019/014673.
Bauer et al., Jan. 15, 2010, Identification of markers of taxane sensitivity using proteomic and genomic analyses of breast tumors from patients receiving neoadjuvant paclitaxel and radiation, Clinical Cancer Research, 16(2):681-690.
Bazhenova, Feb. 21, 2021, Nivolumab in Combination With Plinabulin in Patients With Metastatic Non-Small Cell Lung Cancer (NSCLC), ClinicalTrials.gov, NCT02812667 version 7.
Collins et al., 2014, Lipid tucaresol as an adjuvant for methamphetamine vaccine development, CHemComm, 50:4079-4081.
Fernandez-Tejada et al., 2014, Design, synthesis, and immunologic evaluation of vaccine adjuvant conjugates based on QS-21 and tucaresol, Bioorganic & Medicinal Chemistry, 22:5917-5923.
Fernandez-Tejada et al., 2016, Development of improved vaccine adjuvants based on the saponin natural product QS-21 through chemical synthesis, Accounts of Chemical Research 49:1741-1756.
Fessas et al., 2017, A molecular and preclinical comparsion of the PC-1-targeted t-cell checkpoint inhibitors nivolumab and mebrolizumag, Seminars in Oncology, 44:136-140.
Flanigan et al., Jan. 7, 2011, Melanoma brain metasteses: is it time ro reassess the bias?, Current Problems in Cancer, 35(4):200-210.
Hwang et al., 2019, Heat shock proteins: a dual carrier-adjuvant for an anti-drug vaccine against heroin, Bioorganic & Medicinal Chemistry, 27:125-132.
Januchowski et al., Jan. 2014, Microarray-based detection and expression analysis of extracellular matrix proteins in drug-resistant ovarian cancer cell lines, Oncology Reports, 32:1981-1990.
Kanojia et al., May 2015, βIII-tubulin regulates breast cancer meastases to the brain, Mol Cancer Ther., 14(5):1152-1161.
Malhotra, J., "A Phase I/II Study of Nivolumab, Ipilimumab and Plinabulin in Patients With Recurrent Small Cell Lung Cancer", ClinicalTrials.gov, NCT03575793 version 9, Apr. 15, 2020, <URL: https://clinicaltrials.gov/ct2/history/NCT035757937V_9=View#StudyPageTop>.
Malhotra, J., Abstract 8570: "A phase I trial of plinabulin in combination with nivolumab and ipilimumab in patients with relapsed small cell lung cancer (SCLC): Big Ten Cancer Research Consortium (BTCRC-LUN17-127) study", Journal of Clinical Oncology, vol. 39, No. 15, May 28, 2021, DOI: 10.1200/JCO.2021.39.15_suppl.8570.
Muguruma et al., 2016, Novel Hybrid Compound of a Plinabulin Prodrug with an IgG Binding Peptide for Generating a Tumor Selective Noncovalent-Type Antibody-Drug Conjugate; Bioconjugate Chem. 27(7):1606-1613.
Nereus Pharmaceuticals, Inc., Aug. 16, 2011, Phase 1/2 study of vascular disrupting agent NPI-2358 + docetaxel in patients with advanced non-small cell lung cancer, ClinicalTrials.gov, NCT00630110 <URL: https://www.clinicaltrials.gov/ct2/show/NCT00630110>.
Snegovoy AV, et al. Practical recommendations for the appointment of colony-stimulating factors in order to prevent the development of febrile neuropathy in cancer patients // Practical recommendations. Version 2016. p. 394-401.
Valet et al., Dec. 2013, Challenging single- and multi-probesets gene expression signatures of pathological complete response to neoadjuvant chemotherapy in breast cancer: experience of the REMAGUS 02 phase II trial, Breast, 22(6):1052-1059.
Zacharie et al., 1997, Regioselective synthesis of 6-substituted 2-hydroxybenzaldehyde: efficient synthesis of the immunomodulator tucaresol and related analogues, Journal of the Chemical Society, 19:2925-2929.
Du et al., Jul. 2018, docetaxel increases the risk of severe infections in the treatment of non-small cell lung cancer: a meta-analysis, Oncosciene, 5(7-8):220-238.
Plunkett et al., Aug. 1995, Gemcitabine: metabolism, mechanisms of action, and self-potentiation, Semin Oncol., 22(4 Suppl 11):3-10.

\* cited by examiner

COMPOSITION AND METHOD FOR REDUCING THROMBOCYTOPENIA

CROSS-REFERENCE TO RELATED APPLICATIONS

This application is a 371 of international PCT Application No. PCT/US2019/014673, filed on Jan. 23, 2019, which claims benefit of U.S. Provisional Application No. 62/718,814, filed on Aug. 14, 2018, and U.S. Provisional Application No. 62/621,543, filed on Jan. 24, 2018, the disclosures of which are incorporated herein by reference in their entireties.

BACKGROUND

Field

The present invention relates to the field of chemistry and medicine. More specifically, it relates to method of reducing or ameliorating thrombocytopenia using Plinabulin.

Description of the Related Art

Platelets, also referred to as thrombocytes, are anuclear cell fragments that exist in mammalian blood and mediate blood clot formation and hemostasis. In addition, platelets release growth factors that play a significant role in the repair and regeneration of connective tissues and facilitate wound healing. Platelets have an average lifespan of about 5 to 10 days, and their physiological blood level in humans is normally 150,000 to 450,000/uL. When a patient's levels of circulating platelets are depleted below the physiological range, this condition is known as thrombocytopenia.

Thrombocytopenia is typically associated with defective formation of hemostatic plugs and bleeding, wherein the risk of bleeding is inversely proportional to the platelet count. For cancer patients, severe thrombocytopenia often necessitates modification of the chemotherapy regimen, thereby compromising the ultimate success of the anticancer treatment plan. Therefore, there is a need for developing drug effective in treating thrombocytopenia.

SUMMARY OF THE INVENTION

Some embodiments relate to a method of reducing thrombocytopenia, comprising administering plinabulin or a pharmaceutically acceptable salt thereof to a subject in need thereof.

Some embodiments relate to a method of increasing platelet production in a subject, comprising administering plinabulin or a pharmaceutically acceptable salt thereof to a subject in need thereof.

Some embodiments relate to a method of stimulating platelet production in a subject, comprising administering plinabulin or a pharmaceutically acceptable salt thereof to a subject in need thereof.

Some embodiments relate to a method of maintaining platelet count at a normal level in a subject receiving a chemotherapy or radiation therapy, comprising administering plinabulin or a pharmaceutically acceptable salt thereof to a subject in need thereof.

Some embodiments relate to a method of reducing the incidence of thrombocytopenia in a subject, comprising administering plinabulin or a pharmaceutically acceptable salt thereof to the subject in need thereof.

Some embodiments relate to method of increasing platelet count in a patient receiving a chemotherapeutic treatment, comprising administering plinabulin or a pharmaceutically acceptable salt thereof to the subject in need thereof.

Some embodiments relate to a method of preventing thrombocytopenia in a subject receiving a chemotherapeutic treatment, comprising administering plinabulin or a pharmaceutically acceptable salt thereof to the subject in need thereof.

Some embodiments relate to a method of increasing platelet count in a subject administered gemcitabine, comprising administering plinabulin or a pharmaceutically acceptable salt thereof to a subject in need thereof.

Some embodiments relate to a method of treating gemcitabine induced thrombocytopenia in a subject, comprising: identifying a patient having a breast cancer, ovarian cancer, non-small cell lung cancer, pancreatic cancer, or bladder cancer; and administering plinabulin at a dose in the range of about 1 mg/m$^2$ to about 50 mg/m$^2$.

Some embodiments relate to a method of stimulating platelet survival, comprising administering plinabulin at a dose in the range of about 1 mg/m$^2$ to about 50 mg/m$^2$.

Some embodiments relate to a pharmaceutical composition comprising about 1 mg to about 100 mg of plinabulin.

Some embodiments relate to a sterile container comprising a gemcitabine, and about 1 mg to about 100 mg of plinabulin, wherein the gemcitabine and the plinabulin are provided in two separate sterile containers.

DETAILED DESCRIPTION OF THE PREFERRED EMBODIMENT

Figure 1:
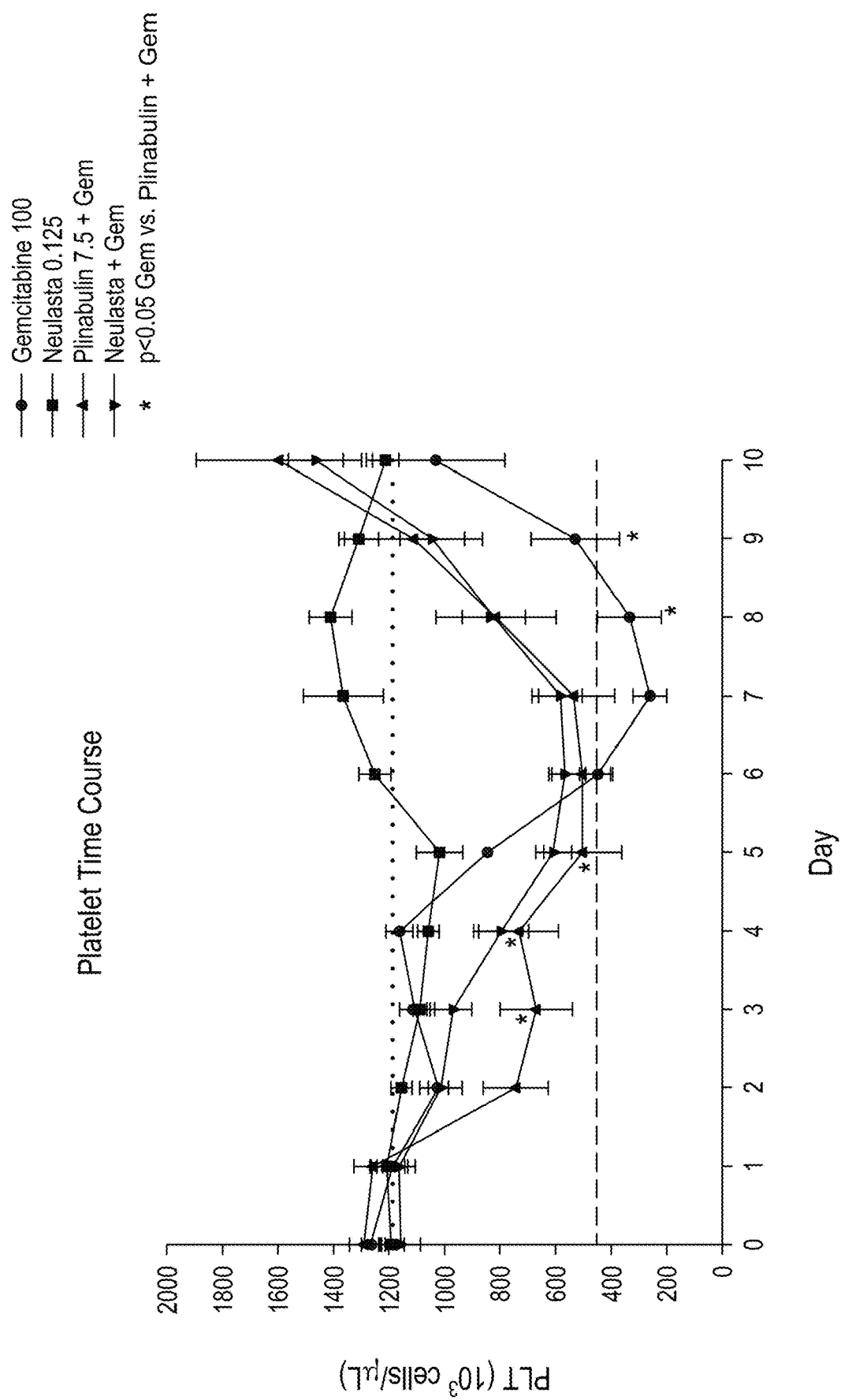
FIG. 1 shows the effect of plinabulin and pegfilgrastim on gemcitabine-induced hematological effects.

Some embodiments relate to a method of reducing the incidence of thrombocytopenia, comprising administering plinabulin or a pharmaceutically acceptable salt thereof to a subject in need thereof.

In some embodiments, the thrombocytopenia is induced by administration of one or more chemotherapeutic agents or by administration of radiation therapy.

In some embodiments, the thrombocytopenia is induced by administration of one or more chemotherapeutic agents.

In some embodiments, the thrombocytopenia is induced by administration of gemcitabine or a chemotherapeutic composition comprising gemcitabine.

Some embodiments relate to a method of increasing platelet count in a patient receiving a chemotherapeutic treatment, comprising administering plinabulin or a pharmaceutically acceptable salt thereof to the subject in need thereof.

Some embodiments relate to a method of preventing thrombocytopenia in a subject receiving a chemotherapeutic treatment, comprising administering plinabulin or a pharmaceutically acceptable salt thereof to the subject in need thereof.

Some embodiments relate to a method of increasing platelet count in a subject administered gemcitabine, comprising administering plinabulin or a pharmaceutically acceptable salt thereof to a subject in need thereof.

Some embodiments relate to a method of treating gemcitabine induced thrombocytopenia in a subject, comprising: identifying a patient having a breast cancer, ovarian cancer, non-small cell lung cancer, pancreatic cancer, or bladder cancer; and administering plinabulin at a dose in the range of about 1 mg/m$^2$ to about 50 mg/m$^2$.

Thrombocytopenia can be categorized according to the National Cancer Institute common terminology criteria (NCI-CTC). The normal platelet count for patient ranges from $150\times10^3$ to $400\times10^3$/mL. In some embodiments, thrombocytodenia is diagnosed when the platelet count is $<150\times10^3$/mL. In some embodiments, thrombocytopenia has been classified into 4 grades: grade 1:75,000 to 149,000/mL, grade 2:50,000 to 74,000/mL, grade 3: 25,000 to 49,000/mL; and grade 4: <25,000/mL In some embodiments, thrombocytopenia was classified as mild (platelet count Z100 and $<150\times10^9$/L), moderate (platelet count≥50 and $<100\times10^9$/L), and severe (platelet count$<50\times10^9$/L).

In some embodiments, the patient has an advanced or metastatic breast cancer, early stage breast cancer, non-small cell lung cancer, refractory metastatic prostate cancer. In some embodiments, the patient has head and neck cancer, lung cancer, stomach cancer, colon cancer, pancreatic cancer, prostate cancer, breast cancer, kidney cancer, bladder cancer, ovary cancer, cervical cancer, melanoma, glioblastoma, myeloid leukemia, myeloma, lymphoma, or leukemia. In some embodiments, the patient has renal cell carcinoma, malignant melanoma, non-small cell lung cancer (NSCLC), ovarian cancer, Hodgkin's lymphoma or squamous cell carcinoma. In some embodiments, the patient has breast cancer, colon cancer, rectal cancer, lung cancer, prostate cancer, melanoma, leukemia, ovarian cancer, gastric cancer, renal cell carcinoma, liver cancer, pancreatic cancer, lymphomas and myeloma. In some embodiments, the patient has a solid tumor or hematological cancer. In some embodiments, the patient has Acute Lymphocytic Leukemia (ALL), Acute Myeloid Leukemia (AML), Adrenal Cancer, Basal and Squamous Cell Skin Cancer, Bile Duct Cancer, Bladder Cancer, Bone Cancer, Brain and Spinal Cord Tumors, Breast Cancer, Cervical Cancer, Chronic Lymphocytic Leukemia (CLL), Chronic Myeloid Leukemia (CML), Chronic Myelomonocytic Leukemia (CMML), Colorectal Cancer, Endometrial Cancer, Esophagus Cancer, eye Cancer (Ocular Melanoma and Lymphoma), Gallbladder Cancer, Gastrointestinal Carcinoid Tumors, Gastrointestinal Stromal Tumor (GIST), Gestational Trophoblastic Disease, Hodgkin Lymphoma, Kaposi Sarcoma, Kidney Cancer, Laryngeal and Hypopharyngeal Cancer, Leukemia, Liver Cancer, Lung Cancer, Lung Carcinoid Tumor, Lymphoma, Malignant Mesothelioma, Melanoma Skin Cancer, Merkel Cell Skin Cancer, Multiple Myeloma, Myelodysplastic Syndromes, Nasal Cavity and Paranasal Sinuses Cancer, Nasopharyngeal Cancer, Neuroblastoma, Non-Hodgkin Lymphoma, Non-Small Cell Lung Cancer, Oral Cavity and Oropharyngeal Cancer, Osteosarcoma, Ovarian Cancer, Pancreatic Cancer, Prostate Cancer, Retinoblastoma, Rhabdomyosarcoma, Salivary Gland Cancer, Skin Cancer, Small Cell Lung Cancer, Small Intestine Cancer, Soft Tissue Sarcoma, Stomach Cancer, Testicular Cancer, Thymus Cancer, Thyroid Cancer, Uterine Sarcoma, Vaginal Cancer, Vulvar Cancer, Waldenstrom Macroglobulinemia, or Wilms Tumor.

Some embodiments relate to treating a chemotherapy (e.g., docetaxel, gemcitabine) induced thrombocytopenia in a subject having advanced for metastatic breast cancer, comprising identifying a patient having advanced or metastatic breast cancer at risk for developing thrombocytopenia (e.g. severe thrombocytopenia or grade 3 or 4 thrombocytopenia); and administering a pharmaceutically effective amount of plinabulin.

Some embodiments relate to a method of treating chemotherapy (e.g., docetaxel, gemcitabine, TAC, or TC) thrombocytopenia in a subject having non-small cell lung cancer, comprising: identifying a patient having non-small cell lung cancer at risk for developing thrombocytopenia (e.g. severe thrombocytopenia or grade 3 or 4 thrombocytopenia); and administering a pharmaceutically effective amount of plinabulin.

Some embodiments relate to a method of treating chemotherapy (e.g., docetaxel, gemcitabine, TAC, or TC) induced thrombocytopenia in a subject having hormone refractory metastatic prostate cancer, comprising: identifying a patient having hormone refractory metastatic prostate cancer at risk for developing thrombocytopenia (e.g. severe thrombocytopenia or grade 3 or 4 thrombocytopenia); and administering a pharmaceutically effective amount of plinabulin.

In some embodiments, the thrombocytopenia is a grade 3 or 4 thrombocytopenia. In some embodiments, the thrombocytopenia is a drug-induced thrombocytopenia. In some embodiments, the thrombocytopenia is a chemotherapy or radiation therapy induced thrombocytopenia. In some embodiments, the thrombocytopenia is a taxane-induced thrombocytopenia. In some embodiments, the thrombocytopenia is not induced by taxane or a chemotherapeutic composition comprising taxane. In some embodiments, the thrombocytopenia is not induced by docetaxel.

Some embodiments relate to a method of stimulating platelet survival, comprising administering plinabulin at a dose in the range of about 1 mg/m$^2$ to about 50 mg/m$^2$. In some embodiments, the plinabulin is administered at a dose of about 20 mg/m$^2$.

In some embodiments, the subject has a grade 1 thrombocytopenia. In some embodiments, the subject has a grade 2 thrombocytopenia. In some embodiments, the subject has a grade 3 thrombocytopenia. In some embodiments, the subject has a grade 4 thrombocytopenia.

In some embodiments, the subject has a platelet count that is less than 150,000/mm$^3$. In some embodiments, the subject has a platelet count that is less than 75,000/mm$^3$. In some embodiments, the subject has a platelet count that is less than 50,000/mm$^3$. In some embodiments, the subject has a platelet count that is less than 25,000/mm$^3$. In some embodiments, the subject has a platelet count that is less than 150,000/mm$^3$ and greater than 75,000/mm$^3$. In some embodiments, the subject has a platelet count that is less than 75,000/mm$^3$ and greater than 50,000/mm$^3$. In some embodiments, the subject has a platelet count that is less than 50,000/mm$^3$ and greater than 25,000/mm$^3$. In some embodiments, the subject has a platelet count that is less than 25,000/mm$^3$.

In some embodiments, administration of plinabulin helps maintain the platelet count of the patient to be above about 150,000/mm$^3$. In some embodiments, administration of plinabulin helps maintain the platelet count of the patient to be above about 75,000/mm$^3$. In some embodiments, administration of plinabulin helps maintain the platelet count of the patient to be above about 50,000/mm³. In some embodiments, administration of plinabulin helps maintain the platelet count of the patient to be above about 25,000/mm³. In some embodiments, administration of plinabulin helps maintain the platelet count of the patient to be above about 75,000/mm³. In some embodiments, administration of plinabulin helps maintain the platelet count of the patient to be in the range of about 150,000/mm³ to about 450,000/mm³. In some embodiments, administration of plinabulin helps maintain the platelet count of the patient to be in the range of about 100,000/mm³ to about 500,000/mm³. In some embodiments, administration of plinabulin helps maintain the platelet count of the patient to be in the range of about 100,000/mm³ to about 400,000/mm³. In some embodiments, administration of plinabulin helps maintain the platelet count of the patient to be in the range of about 70,000/mm³ to about 450,000/mm³. In some embodiments, administration of plinabulin helps maintain the platelet count of the patient to be in the range of about 70,000/mm³ to about 400,000/mm³.

In some embodiments, the method includes administering gemcitabine. In some embodiments, the method includes administering one or more additional chemotherapeutic compositions to the subject. In some embodiments, the method includes administering a second chemotherapeutic composition. In some embodiments, the method includes administering a third chemotherapeutic composition. In some embodiments, the method includes administering a fourth chemotherapeutic composition. In some embodiments, the method includes administering a fifth chemotherapeutic composition. In some embodiments, the method includes administering a sixth chemotherapeutic composition. In some embodiments, the method includes administering a seventh chemotherapeutic composition. In some embodiments, the method includes administering an eighth chemotherapeutic composition. In some embodiments, the first chemotherapeutic composition and each of the additional chemotherapeutic compositions are different. In some embodiments, the first chemotherapeutic composition and at least one of the additional chemotherapeutic compositions are the same. In some embodiments, the first chemotherapeutic composition is the same as the second, the third, the fourth, the fifth, the sixth, the seventh, or the eighth chemotherapeutic composition. In some embodiments, the first chemotherapeutic composition is different from the second, the third, the fourth, the fifth, the sixth, the seventh, or the eighth chemotherapeutic composition.

In some embodiments, the method described herein can include administering one or more chemotherapeutic compositions. In some embodiments, the one or more chemotherapeutic composition can be administered after the administration of plinabulin. In some embodiments, the one or more chemotherapeutic composition can be administered before the administration of plinabulin. In some embodiments, the one or more chemotherapeutic composition can be administered simultaneously with plinabulin.

In some embodiments, the one or more additional chemotherapeutic compositions (e.g., the second, third, fourth, fifth, sixth, seventh, or eighth chemotherapeutic composition) can independently include one or more agents selected from the group consisting of methotrexate, vinblastine, doxorubicin, cisplatin, MVAC, docetaxel, trastuzumab, cyclophosphamide, paclitaxel, dose-dense AC followed by T (i.e., doxorubicin, cyclophosphamide, paclitaxel), TAC (docetaxel, doxorubicin, cyclophosphamide), fluorouracil, bleomycin, etoposide, vincristine, procarbazine, prednisone, BEACOPP (bleomycin, etoposide, doxorubicin, cyclophosphamide, vincristine, procarbazine, prednisone), gemcitabine, ifosfamide, carboplatin, ICE (ifosfamide, carboplatin, etoposide), rituximab, RICE (rituximab, ifosfamide, carboplatin, etoposide), CHOP-14 (cyclophosphamide, doxorubicin, vincristine, prednisone), mesna, novantrone, MINE (mesna, ifosfamide, novantrone, etoposide), dexamethasone, cytarabine DHAP (dexamethasone, cisplatin, cytarabine), methylprednisolone, ESHAP (etoposide, methylprednisolone, cisplatin, cytarabine), HyperCVAD and rituximab (cyclophosphamide, vincristine, doxorubicin, dexamethasone, rituximab), dacarbazine, vinblastine, dacarbazine-based combination (dacarbazine, cisplatin, vinblastine), dacarbazine-based combination with IL-2 and interferon alfa (dacarbazine, cisplatin, vinblastine, IL-2, interferon alfa), topotecan, MAID (mesna, doxorubicin, ifosfamine, dacarbazine), VeIP (vinblastine, ifosfamide, cisplatin), VIP (etoposide, ifosfamide, cisplatin), TIP (paclitaxel, ifosfamide, cisplatin), gemcitabine, CMF classic (cyclophosphamide, methotrexate, fluorouracil), AC (doxorubicin, cyclophosphamide), FEC (fluorouracil, epirubicin, cyclophosphamide), TC (docetaxel, cyclophosphamide), cisplatin/topotecan, paclitaxel/cisplatin, irincotecan, FOLFOX (fluorouracil, leucovorin, oxaliplatin), irincotecan/cisplatin, epirubicin/cisplatin/5-fluorouracil, epirubicin/cisplatin/capecitabine, DT-PACE (dexamethasone/thalidomide/cisplatin/doxorubicin/cyclophosphamide/etoposide), ET-PACE and bortezomib, EPOCH (etoposide, prednisone, vincristine, cyclophosphamide, doxorubicin), GDP (gemcitabine, dexamethasone, cisplatin), GDP and rituximab, FMR (fludarabine, mitoxantrone, rituximab, CHOP and rituximab (cyclophosphamide, doxorubicin, vincristine, prednisone, rituximab), cisplatin/paclitaxel, cisplatin/vinorelbine, cisplatin/docetaxel, ciaplatin/etoposide, carboplatin/paclitaxel, carboplatin/docetaxel, FOLFIRINOX, cabazitaxel, etoposide/carboplatin, etoposide/cisplatin. In some embodiments, the one or more additional chemotherapeutic compositions (e.g., the second, third, fourth, fifth, sixth, seventh, or eighth chemotherapeutic composition) can independently include one or more agents selected from the group consisting of methotrexate, vinblastine, doxorubicin, cisplatin, docetaxel, trastuzumab, cyclophosphamide, paclitaxel, fluorouracil, bleomycin, etoposide, vincristine, procarbazine, prednisone, ifosfamide, carboplatin, mesna, novantrone, cytarabine methylprednisolone, rituximab dacarbazine, vinblastine, topotecan, gemcitabine, irincotecan, epirubicin, 5-fluorouracil, capecitabine, bortezomib, and cabazitaxel.

Some embodiments relate to a method of stimulating platelet survival, comprising administering plinabulin at a dose in the range of about 1 mg/m² to about 50 mg/m². In some embodiments, the plinabulin is administered at a dose in the range of about 1-50 mg/m² of the body surface area. In some embodiments, the plinabulin is administered at a dose in the range of about 1-2, 1-3, 1-4, 1-5, 1-6, 1-7, 1-8, 1-9, 1-10, 1-11, 1-12, 1-13, 1-13.75, 1-14, 1-15, 1-16, 1-17, 1-18, 1-19, 1-20, 1-22.5, 1-25, 1-27.5, 1-30, 1.5-2, 1.5-3, 1.5-4, 1.5-5, 1.5-6, 1.5-7, 1.5-8, 1.5-9, 1.5-10, 1.5-11, 1.5-12, 1.5-13, 1.5-13.75, 1.5-14, 1.5-15, 1.5-16, 1.5-17, 1.5-18, 1.5-19, 1.5-20, 1.5-22.5, 1.5-25, 1.5-27.5, 1.5-30, 2.5-2, 2.5-3, 2.5-4, 2.5-5, 2.5-6, 2.5-7, 2.5-8, 2.5-9, 2.5-10, 2.5-11, 2.5-12, 2.5-13, 2.5-13.75, 2.5-14, 2.5-15, 2.5-16, 2.5-17, 2.5-18, 2.5-19, 2.5-20, 2.5-22.5, 2.5-25, 2.5-27.5, 2.5-30, 2.5-7.5, 3-4, 3-5, 3-6, 3-7, 3-8, 3-9, 3-10, 3-11, 3-12, 3-13, 3-13.75, 3-14, 3-15, 3-16, 3-17, 3-18, 3-19, 3-20, 3-22.5, 3-25, 3-27.5, 3-30, 3.5-6.5, 3.5-13.75, 3.5-15, 2.5-17.5, 4-5, 4-6, 4-7, 4-8, 4-9, 4-10, 4-11, 4-12, 4-13, 4-13.75, 4-14, 4-15, 4-16, 4-17, 4-18, 4-19, 4-20, 4-22.5, 4-25, 4-27.5, 4-30, 5-6, 5-7, 5-8, 5-9, 5-10, 5-11, 5-12, 5-13, 5-13.75, 5-14, 5-15, 5-16, 5-17, 5-18, 5-19, 5-20, 5-22.5, 5-25, 5-27.5, 5-30, 6-7, 6-8, 6-9, 6-10, 6-11, 6-12, 6-13, 6-13.75, 6-14, 6-15, 6-16, 6-17, 6-18, 6-19, 6-20, 6-22.5, 6-25, 6-27.5, 6-30, 7-8, 7-9, 7-10, 7-11, 7-12, 7-13, 7-13.75, 7-14, 7-15, 7-16, 7-17, 7-18, 7-19, 7-20, 7-22.5, 7-25, 7-27.5, 7-30, 7.5-12.5, 7.5-13.5, 7.5-15, 8-9, 8-10, 8-11, 8-12, 8-13, 8-13.75, 8-14, 8-15, 8-16, 8-17, 8-18, 8-19, 8-20, 8-22.5, 8-25, 8-27.5, 8-30, 9-10, 9-11, 9-12, 9-13, 9-13.75, 9-14, 9-15, 9-16, 9-17, 9-18, 9-19, 9-20, 9-22.5, 9-25, 9-27.5, 9-30, 10-11, 10-12, 10-13, 10-13.75, 10-14, 10-15, 10-16, 10-17, 10-18, 10-19, 10-20, 10-22.5, 10-25, 10-27.5, 10-30, 11.5-15.5, 12.5-14.5, 7.5-22.5, 8.5-32.5, 9.5-15.5, 15.5-24.5, 5-35, 17.5-22.5, 22.5-32.5, 25-35, 25.5-24.5, 27.5-32.5, 2-20, t 2.5-22.5, or 9.5-21.5 mg/m$^2$, of the body surface area. In some embodiments, the plinabulin is administered at a dose of about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40 mg/m$^2$ of the body surface area. In some embodiments, the plinabulin is administered at a dose less than about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40 mg/m$^2$ of the body surface area. In some embodiments, the plinabulin is administered at a dose greater than about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40, 41, 42, 43, 44, 45, 46, 47, 48, 49, 50 mg/m$^2$ of the body surface area.

In some embodiments, the plinabulin dose is about 5 mg-300 mg, 5 mg-200 mg, 7.5 mg-200 mg, 10 mg-100 mg, 15 mg-100 mg, 20 mg-100 mg, 30 mg-100 mg, 40 mg-100 mg, 10 mg-80 mg, 15 mg-80 mg, 20 mg-80 mg, 30 mg-80 mg, 40 mg-80 mg, 10 mg-60 mg, 15 mg-60 mg, 20 mg-60 mg, 30 mg-60 mg, or about 40 mg-60 mg. In some embodiments, the plinabulin administered is about 20 mg-60 mg, 27 mg-60 mg, 20 mg-45 mg, or 27 mg-45 mg. In some embodiments, the plinabulin administered is about 5 mg-7.5 mg, 5 mg-9 mg, 5 mg-10 mg, 5 mg-12 mg, 5 mg-14 mg, 5 mg-15 mg, 5 mg-16 mg, 5 mg-18 mg, 5 mg-20 mg, 5 mg-22 mg, 5 mg-24 mg, 5 mg-26 mg, 5 mg-28 mg, 5 mg-30 mg, 5 mg-32 mg, 5 mg-34 mg, 5 mg-36 mg, 5 mg-38 mg, 5 mg-40 mg, 5 mg-42 mg, 5 mg-44 mg, 5 mg-46 mg, 5 mg-48 mg, 5 mg-50 mg, 5 mg-52 mg, 5 mg-54 mg, 5 mg-56 mg, 5 mg-58 mg, 5 mg-60 mg, 7 mg-7.7 mg, 7 mg-9 mg, 7 mg-10 mg, 7 mg-12 mg, 7 mg-14 mg, 7 mg-15 mg, 7 mg-16 mg, 7 mg-18 mg, 7 mg-20 mg, 7 mg-22 mg, 7 mg-24 mg, 7 mg-26 mg, 7 mg-28 mg, 7 mg-30 mg, 7 mg-32 mg, 7 mg-34 mg, 7 mg-36 mg, 7 mg-38 mg, 7 mg-40 mg, 7 mg-42 mg, 7 mg-44 mg, 7 mg-46 mg, 7 mg-48 mg, 7 mg-50 mg, 7 mg-52 mg, 7 mg-54 mg, 7 mg-56 mg, 7 mg-58 mg, 7 mg-60 mg, 9 mg-10 mg, 9 mg-12 mg, 9 mg-14 mg, 9 mg-15 mg, 9 mg-16 mg, 9 mg-18 mg, 9 mg-20 mg, 9 mg-22 mg, 9 mg-24 mg, 9 mg-26 mg, 9 mg-28 mg, 9 mg-30 mg, 9 mg-32 mg, 9 mg-34 mg, 9 mg-36 mg, 9 mg-38 mg, 9 mg-40 mg, 9 mg-42 mg, 9 mg-44 mg, 9 mg-46 mg, 9 mg-48 mg, 9 mg-50 mg, 9 mg-52 mg, 9 mg-54 mg, 9 mg-56 mg, 9 mg-58 mg, 9 mg-60 mg, 10 mg-12 mg, 10 mg-14 mg, 10 mg-15 mg, 10 mg-16 mg, 10 mg-18 mg, 10 mg-20 mg, 10 mg-22 mg, 10 mg-24 mg, 10 mg-26 mg, 10 mg-28 mg, 10 mg-30 mg, 10 mg-32 mg, 10 mg-34 mg, 10 mg-36 mg, 10 mg-38 mg, 10 mg-40 mg, 10 mg-42 mg, 10 mg-44 mg, 10 mg-46 mg, 10 mg-48 mg, 10 mg-50 mg, 10 mg-52 mg, 10 mg-54 mg, 10 mg-56 mg, 10 mg-58 mg, 10 mg-60 mg, 12 mg-14 mg, 12 mg-15 mg, 12 mg-16 mg, 12 mg-18 mg, 12 mg-20 mg, 12 mg-22 mg, 12 mg-24 mg, 12 mg-26 mg, 12 mg-28 mg, 12 mg-30 mg, 12 mg-32 mg, 12 mg-34 mg, 12 mg-36 mg, 12 mg-38 mg, 12 mg-40 mg, 12 mg-42 mg, 12 mg-44 mg, 12 mg-46 mg, 12 mg-48 mg, 12 mg-50 mg, 12 mg-52 mg, 12 mg-54 mg, 12 mg-56 mg, 12 mg-58 mg, 12 mg-60 mg, 15 mg-16 mg, 15 mg-18 mg, 15 mg-20 mg, 15 mg-22 mg, 15 mg-24 mg, 15 mg-26 mg, 15 mg-28 mg, 15 mg-30 mg, 15 mg-32 mg, 15 mg-34 mg, 15 mg-36 mg, 15 mg-38 mg, 15 mg-40 mg, 15 mg-42 mg, 15 mg-44 mg, 15 mg-46 mg, 15 mg-48 mg, 15 mg-50 mg, 15 mg-52 mg, 15 mg-54 mg, 15 mg-56 mg, 15 mg-58 mg, 15 mg-60 mg, 17 mg-18 mg, 17 mg-20 mg, 17 mg-22 mg, 17 mg-24 mg, 17 mg-26 mg, 17 mg-28 mg, 17 mg-30 mg, 17 mg-32 mg, 17 mg-34 mg, 17 mg-36 mg, 17 mg-38 mg, 17 mg-40 mg, 17 mg-42 mg, 17 mg-44 mg, 17 mg-46 mg, 17 mg-48 mg, 17 mg-50 mg, 17 mg-52 mg, 17 mg-54 mg, 17 mg-56 mg, 17 mg-58 mg, 17 mg-60 mg, 20 mg-22 mg, 20 mg-24 mg, 20 mg-26 mg, 20 mg-28 mg, 20 mg-30 mg, 20 mg-32 mg, 20 mg-34 mg, 20 mg-36 mg, 20 mg-38 mg, 20 mg-40 mg, 20 mg-42 mg, 20 mg-44 mg, 20 mg-46 mg, 20 mg-48 mg, 20 mg-50 mg, 20 mg-52 mg, 20 mg-54 mg, 20 mg-56 mg, 20 mg-58 mg, 20 mg-60 mg, 22 mg-24 mg, 22 mg-26 mg, 22 mg-28 mg, 22 mg-30 mg, 22 mg-32 mg, 22 mg-34 mg, 22 mg-36 mg, 22 mg-38 mg, 22 mg-40 mg, 22 mg-42 mg, 22 mg-44 mg, 22 mg-46 mg, 22 mg-48 mg, 22 mg-50 mg, 22 mg-52 mg, 22 mg-54 mg, 22 mg-56 mg, 22 mg-58 mg, 22 mg-60 mg, 25 mg-26 mg, 25 mg-28 mg, 25 mg-30 mg, 25 mg-32 mg, 25 mg-34 mg, 25 mg-36 mg, 25 mg-38 mg, 25 mg-40 mg, 25 mg-42 mg, 25 mg-44 mg, 25 mg-46 mg, 25 mg-48 mg, 25 mg-50 mg, 25 mg-52 mg, 25 mg-54 mg, 25 mg-56 mg, 25 mg-58 mg, 25 mg-60 mg, 27 mg-28 mg, 27 mg-30 mg, 27 mg-32 mg, 27 mg-34 mg, 27 mg-36 mg, 27 mg-38 mg, 27 mg-40 mg, 27 mg-42 mg, 27 mg-44 mg, 27 mg-46 mg, 27 mg-48 mg, 27 mg-50 mg, 27 mg-52 mg, 27 mg-54 mg, 27 mg-56 mg, 27 mg-58 mg, 27 mg-60 mg, 30 mg-32 mg, 30 mg-34 mg, 30 mg-36 mg, 30 mg-38 mg, 30 mg-40 mg, 30 mg-42 mg, 30 mg-44 mg, 30 mg-46 mg, 30 mg-48 mg, 30 mg-50 mg, 30 mg-52 mg, 30 mg-54 mg, 30 mg-56 mg, 30 mg-58 mg, 30 mg-60 mg, 33 mg-34 mg, 33 mg-36 mg, 33 mg-38 mg, 33 mg-40 mg, 33 mg-42 mg, 33 mg-44 mg, 33 mg-46 mg, 33 mg-48 mg, 33 mg-50 mg, 33 mg-52 mg, 33 mg-54 mg, 33 mg-56 mg, 33 mg-58 mg, 33 mg-60 mg, 36 mg-38 mg, 36 mg-40 mg, 36 mg-42 mg, 36 mg-44 mg, 36 mg-46 mg, 36 mg-48 mg, 36 mg-50 mg, 36 mg-52 mg, 36 mg-54 mg, 36 mg-56 mg, 36 mg-58 mg, 36 mg-60 mg, 40 mg-42 mg, 40 mg-44 mg, 40 mg-46 mg, 40 mg-48 mg, 40 mg-50 mg, 40 mg-52 mg, 40 mg-54 mg, 40 mg-56 mg, 40 mg-58 mg, 40 mg-60 mg, 43 mg-46 mg, 43 mg-48 mg, 43 mg-50 mg, 43 mg-52 mg, 43 mg-54 mg, 43 mg-56 mg, 43 mg-58 mg, 42 mg-60 mg, 45 mg-48 mg, 45 mg-50 mg, 45 mg-52 mg, 45 mg-54 mg, 45 mg-56 mg, 45 mg-58 mg, 45 mg-60 mg, 48 mg-50 mg, 48 mg-52 mg, 48 mg-54 mg, 48 mg-56 mg, 48 mg-58 mg, 48 mg-60 mg, 50 mg-52 mg, 50 mg-54 mg, 50 mg-56 mg, 50 mg-58 mg, 50 mg-60 mg, 52 mg-54 mg, 52 mg-56 mg, 52 mg-58 mg, or 52 mg-60 mg. In some embodiments, the plinabulin dose is greater than about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg. In some embodiments, the plinabulin dose is about less than about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg.

The chemotherapeutic composition or chemotherapeutic agent can be administered in an effective amount suitable for the treatment. In some embodiments, the method described herein comprises administering one or more chemotherapeutic agents (e.g., gemcitabine) at a dose in the range of about 40-50 mg/kg in divided doses over 2-5 days. In some embodiments, the method described herein comprises administering one or more chemotherapeutic agents at a dose in the range of about 10-30, 5-100, 10-200, 10-100, 10-90, 10-80, 10-70, 10-60, 10-50, 10-40, 10-30, 10-20, 20-200, 20-100, 20-90, 20-80, 20-70, 20-60, 20-50, 20-40, 20-30, 30-200, 30-100, 30-90, 30-80, 30-70, 30-60, 30-50, 30-40, 40-200, 40-100, 40-90, 40-80, 40-70, 40-60, 40-50, 50-300, 50-200, 50-100, 50-90, 50-80, 50-70, 50-60, 60-300, 60-200, 60-100, 60-90, 60-80, 60-70, 70-300, 70-200, 70-100, 70-90, 70-80, 80-300, 80-200, 80-100, 80-90, or 90-300, 90-200, 90-100, 100-500, 100-400, 100-300, or 100-200 mg/kg over 2-5 days per cycle. In some embodiments, the method described herein comprises administering one or more chemotherapeutic agents at a dose in the range of about 10-15 mg/kg in divided doses over 7-10 days or 3-5 mg/kg twice weekly. In some embodiments, the method described herein comprises administering one or more chemotherapeutic agents at a dose in the range of about 10-30, 5-100, 10-200, 10-100, 10-90, 10-80, 10-70, 10-60, 10-50, 10-40, 10-30, 10-20, 20-200, 20-100, 20-90, 20-80, 20-70, 20-60, 20-50, 20-40, 20-30, 30-200, 30-100, 30-90, 30-80, 30-70, 30-60, 30-50, 30-40, 40-200, 40-100, 40-90, 40-80, 40-70, 40-60, 40-50, 50-300, 50-200, 50-100, 50-90, 50-80, 50-70, 50-60, 60-300, 60-200, 60-100, 60-90, 60-80, 60-70, 70-300, 70-200, 70-100, 70-90, 70-80, 80-300, 80-200, 80-100, 80-90, or 90-300, 90-200, 90-100, 100-500, 100-400, 100-300, or 100-200 mg/kg twice weekly. In some embodiments, the method described herein comprises administering one or more chemotherapeutic agents at a dose in the range of about 1-5 mg/kg per day for both initial dose and maintenance dose.

In some embodiments, the method further comprises administering (e.g., gemcitabine) at a dose in the range of about 500 to about 1500 mg/m$^2$. In some embodiments, the method the method further comprises administering (e.g., gemcitabine) at a dose in the range of about 900 to about 1300 mg/m$^2$. In some embodiments, the method further comprises administering (e.g., gemcitabine) at a dose in the range of about 500 to about 1500 mg/m$^2$. In some embodiments, the method further comprises administering (e.g., gemcitabine) at a dose about 1000 mg/m$^2$. In some embodiments, the method further comprises administering (e.g., gemcitabine) at a dose about 1250 mg/m$^2$. In some embodiments, the gemcitabine is administered on day 1 and 8 of each 21-day cycle. In some embodiments, the gemcitabine is administered on day 1, 8, and 15 of each 21-day cycle. In some embodiments, the gemcitabine is administered daily for a week. In some embodiments, the gemcitabine is administered once a week for seven weeks, then a week rest, then once weekly for three weeks.

In some embodiments, the method further comprises administering one or more chemotherapeutic agents (e.g., gemcitabine) at a dose in the range of about 10-30, 5-100, 10-200, 10-100, 10-90, 10-80, 10-70, 10-60, 10-50, 10-40, 10-30, 10-20, 20-200, 20-100, 20-90, 20-80, 20-70, 20-60, 20-50, 20-40, 20-30, 30-200, 30-100, 30-90, 30-80, 30-70, 30-60, 30-50, 30-40, 40-200, 40-100, 40-90, 40-80, 40-70, 40-60, 40-50, 50-300, 50-200, 50-100, 50-90, 50-80, 50-70, 50-60, 60-300, 60-200, 60-100, 60-90, 60-80, 60-70, 70-300, 70-200, 70-100, 70-90, 70-80, 80-300, 80-200, 80-100, 80-90, or 90-300, 90-200, 90-100, 100-500, 100-400, 100-300, or 100-200 mg/m$^2$ daily for 5 days per cycle. In some embodiments, the method further comprises administering one or more chemotherapeutic agents at a dose of 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900 or 1000 mg/m$^2$ per cycle once every 4 weeks. In some embodiments, the method further comprises administering one or more chemotherapeutic agents at a dose of 10-30, 5-100, 10-200, 10-100, 10-90, 10-80, 10-70, 10-60, 10-50, 10-40, 10-30, 10-20, 20-200, 20-100, 20-90, 20-80, 20-70, 20-60, 20-50, 20-40, 20-30, 30-200, 30-100, 30-90, 30-80, 30-70, 30-60, 30-50, 30-40, 40-200, 40-100, 40-90, 40-80, 40-70, 40-60, 40-50, 50-300, 50-200, 50-100, 50-90, 50-80, 50-70, 50-60, 60-300, 60-200, 60-100, 60-90, 60-80, 60-70, 70-300, 70-200, 70-100, 70-90, 70-80, 80-300, 80-200, 80-100, 80-90, or 90-300, 90-200, 90-100, 100-500, 100-400, 100-300, or 100-2000 mg/m$^2$ per cycle once every 3 to 4 weeks depending on the extent of prior exposure to radiation therapy and/or prior chemotherapy. In some embodiments, the method further comprises administering one or more chemotherapeutic agents at a dose of 50 mg/m$^2$ per cycle repeated every 4 weeks. In some embodiments, the method further comprises administering one or more chemotherapeutic agents (e.g., cisplatin) at a dose in the range of about 10-30, 5-100, 10-200, 10-100, 10-90, 10-80, 10-70, 10-60, 10-50, 10-40, 10-30, 10-20, 20-200, 20-100, 20-90, 20-80, 20-70, 20-60, 20-50, 20-40, 20-30, 30-200, 30-100, 30-90, 30-80, 30-70, 30-60, 30-50, 30-40, 40-200, 40-100, 40-90, 40-80, 40-70, 40-60, 40-50, 50-300, 50-200, 50-100, 50-90, 50-80, 50-70, 50-60, 60-300, 60-200, 60-100, 60-90, 60-80, 60-70, 70-300, 70-200, 70-100, 70-90, 70-80, 80-300, 80-200, 80-100, 80-90, or 90-300, 90-200, 90-100, 100-500, 100-400, 100-300, or 100-2000 mg/m$^2$ per cycle every 3 weeks or every 4 weeks. In some embodiments, the method further comprises administering one or more chemotherapeutic agents at a dose of 30-70 or 40-60 mg/m$^2$ per cycle once every 3 weeks or every 4 weeks. In some embodiments, when more than one chemotherapeutic agent is administered to the patient, the dose of each of the chemotherapeutic agent administered can be independently selected from any one of the dose ranges described herein.

In some embodiments, one or more chemotherapeutic agents are administered at an amount of about 10-30, 5-100, 10-500, 10-400, 10-300, 10-200, 10-100, 10-90, 10-80, 10-70, 10-60, 10-50, 10-40, 10-30, 10-20, 20-500, 20-400, 20-300, 20-200, 20-100, 20-90, 20-80, 20-70, 20-60, 20-50, 20-40, 20-30, 30-500, 30-400, 30-300, 30-200, 30-100, 30-90, 30-80, 30-70, 30-60, 30-50, 30-40, 40-500, 40-400, 40-300, 40-200, 40-100, 40-90, 40-80, 40-70, 40-60, 40-50, 50-500, 50-400, 50-300, 50-200, 50-100, 50-90, 50-80, 50-70, 50-60, 60-500, 60-400, 60-300, 60-200, 60-100, 60-90, 60-80, 60-70, 70-500, 70-400, 70-300, 70-200, 70-100, 70-90, 70-80, 80-500, 80-400, 80-300, 80-200, 80-100, 80-90, 90-500, 90-400, 90-300, 90-200, 90-100, 100-500, 100-400, 100-300, or 100-200 mg per dose.

In some embodiments, the plinabulin is administered prior to the administration of the chemotherapeutic agent or chemotherapeutic composition. In some embodiments, the plinabulin is administered concurrently with the chemotherapeutic agent or chemotherapeutic composition. In some embodiments, the plinabulin is administered after the chemotherapeutic agent is administered or chemotherapeutic composition.

In some embodiments, the plinabulin is administered about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, or 12 h after the administration of a chemotherapeutic agent or chemotherapeutic composition. In some embodiments, the plinabulin is administered in less than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h after the administration of a chemotherapeutic agent or chemotherapeutic composition. In some embodiments, the plinabulin is administered in more than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h after the administration of a chemotherapeutic agent or chemotherapeutic composition. In some embodiments, the plinabulin is administered in about 1 min-5 min, 1 min-10 min, 1 min-15 min, 1 min-20 min, 1 min-25 min, 1 min-30 min, 0.25 h-0.5 h, 0.25-0.75 h, 0.25-1 h, 0.5 h-1 h, 0.5 h-2 h, 0.5 h-2.5 h, 1 h-2 h, 1 h-3 h, 1 h-5 h after the administration of a chemotherapeutic agent or chemotherapeutic composition.

In some embodiments, when plinabulin is administered prior to a chemotherapeutic agent or chemotherapeutic composition administration, the plinabulin is administered about 1 min-5 min, 1 min-10 min, 1 min-15 min, 1 min-20 min, 1 min-25 min, 1 min-30 min, 0.25 h-0.5 h, 0.25-0.75 h, 0.25-1 h, 0.5 h-1 h, 0.5 h-2 h, 0.5 h-2.5 h, 1 h-2 h, 1 h-3 h, or 1 h-5 h before the administration of a chemotherapeutic agent or chemotherapeutic composition. In some embodiments, the plinabulin is administered about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, or 12 h before the administration of a chemotherapeutic agent or chemotherapeutic composition. In some embodiments, the plinabulin is administered in less than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h before the administration of a chemotherapeutic agent or chemotherapeutic composition. In some embodiments, the plinabulin is administered in more than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h before the administration of a chemotherapeutic agent or chemotherapeutic composition. In some embodiments, plinabulin is administered about 30 mins before the administration of a chemotherapeutic agent or chemotherapeutic composition.

In some embodiments, the treatment schedule includes co-administration of a chemotherapeutic agent or chemotherapeutic composition and plinabulin on day 1, 8 of each 21-day cycle. In some embodiments, the treatment schedule includes co-administration of a chemotherapeutic agent or chemotherapeutic composition and plinabulin on day 1, 8, 15 of each 21-day cycle. In some embodiments, the treatment schedule includes co-administration of a chemotherapeutic agent or chemotherapeutic composition and plinabulin on day 1 of each 21-day cycle. In some embodiments, the treatment schedule includes co-administration of a chemotherapeutic agent or chemotherapeutic composition and plinabulin on day 1 of each 21-day cycle, and the treatment is repeated for two cycles. In some embodiments, the treatment schedule includes co-administration of a chemotherapeutic agent or chemotherapeutic composition and plinabulin on day 1 of each 21-day cycle, and the treatment is repeated for three cycles. In some embodiments, the treatment schedule includes co-administration of a chemotherapeutic agent or chemotherapeutic composition and plinabulin on day 1 of each 21-day cycle, and the treatment is repeated for four cycles. In some embodiments, the treatment schedule includes co-administration of a chemotherapeutic agent or chemotherapeutic composition and plinabulin on day 1 of each 21-day cycle, and the treatment is repeated for five cycles. In some embodiments, the treatment schedule includes co-administration of a chemotherapeutic agent or chemotherapeutic composition and plinabulin once every 3 weeks. In some embodiments, the treatment schedule includes co-administration of a chemotherapeutic agent or chemotherapeutic composition and plinabulin once every 1 week, 2 weeks, 3 weeks, 4 weeks, 5 weeks, 6 weeks, 7 weeks, or 8 weeks. In some embodiments, the treatment schedule includes co-administration of a chemotherapeutic agent or chemotherapeutic composition and plinabulin two times every 1 week, 2 weeks, 3 weeks, 4 weeks, 5 weeks, 6 weeks, 7 weeks, or 8 weeks. In some embodiments, the treatment schedule includes co-administration of a chemotherapeutic agent or chemotherapeutic composition and plinabulin once every 1 week in a treatment cycle of 1 week, 2 weeks, 3 weeks, 4 weeks, 5 weeks, 6 weeks, 7 weeks, or 8 weeks. In some embodiments, the treatment schedule includes co-administration of a chemotherapeutic agent or chemotherapeutic composition and plinabulin twice every 1 week in a treatment cycle of 1 week, 2 weeks, 3 weeks, 4 weeks, 5 weeks, 6 weeks, 7 weeks, or 8 weeks. In some embodiments, the treatment schedule includes co-administration of a chemotherapeutic agent or chemotherapeutic composition and plinabulin on day 1, day 8, and day 15 of a 21-day treatment cycle. In some embodiments, co-administration of a chemotherapeutic agent or chemotherapeutic composition and plinabulin includes administering the chemotherapeutic agent prior to administering plinabulin. In some embodiments, co-administration of a chemotherapeutic agent or chemotherapeutic composition and plinabulin includes that the chemotherapeutic agent or composition is administered about 30 mins prior to plinabulin administration. In some embodiments, co-administration of a chemotherapeutic agent or chemotherapeutic composition and plinabulin includes that the chemotherapeutic agent or composition is administered about 30 mins to 1 hour prior to plinabulin administration. In some embodiments, co-administration of a chemotherapeutic agent or chemotherapeutic composition and plinabulin includes that the chemotherapeutic agent or composition is administered about 30 mins to 2 hour prior to plinabulin administration. In some embodiments, co-administration of a chemotherapeutic agent or chemotherapeutic composition and plinabulin includes administering the chemotherapeutic agent after administering plinabulin. In some embodiments, co-administration of a chemotherapeutic agent or chemotherapeutic composition and plinabulin includes administering the chemotherapeutic agent concurrently with plinabulin. The chemotherapeutic composition described herein can independently be the first, second, third, fourth, fifth, sixth, seventh, or eighth chemotherapeutic composition. In some embodiments, the treatment schedule includes co-administration of a chemotherapeutic agent or chemotherapeutic composition and plinabulin every day of the week for a week. In some embodiments, the treatment schedule includes co-administration of a chemotherapeutic agent or chemotherapeutic composition and plinabulin every day of the week for 2 weeks, 3 weeks, or 4 weeks. In some embodiments, the treatment schedule includes co-administration of a chemotherapeutic agent or chemotherapeutic composition and plinabulin on day 1 in weekly treatment. In some embodiments, the treatment schedule includes co-administration of a chemotherapeutic agent or chemotherapeutic composition and plinabulin on day 1 and day 2 in weekly treatment. In some embodiments, the treatment schedule includes co-administration of the chemotherapeutic agent or chemotherapeutic composition and plinabulin on day 1, day 2, and day 3 in weekly treatment. In some embodiments, the treatment schedule includes co-administration of the chemotherapeutic agent or chemotherapeutic composition and plinabulin on day 1, day 2, day 3 in weekly treatment. In some embodiments, the treatment schedule includes co-administration of the chemotherapeutic agent or chemotherapeutic composition and plinabulin on day 1, day 2, day 3, and day 4 in weekly treatment. In some embodiments, the treatment schedule includes co-administration of the chemotherapeutic agent or chemotherapeutic composition and plinabulin on day 1, day 2, day 3, day 4, and day 5 in weekly treatment. In some embodiments, the treatment schedule includes co-administration of the chemotherapeutic agent or chemotherapeutic composition and plinabulin on day 1, day 2, day 3, day 4, day 5, and day 6 in weekly treatment. In some embodiments, the treatment schedule includes co-administration of a chemotherapeutic agent or chemotherapeutic composition and plinabulin on day 1, day 3, and day 5 in weekly treatment. In some embodiments, the chemotherapeutic composition used on each administration day can be the same or different. In some embodiments, the chemotherapeutic composition used on the first administration day is different from the chemotherapeutic composition used on the rest of the administration days. In some embodiments, the chemotherapeutic composition used on the first administration day is the same as or different from the chemotherapeutic composition used on the second administration day. In some embodiments, the chemotherapeutic composition used on the first administration day is the same as or different from the chemotherapeutic composition used on the third administration day. In some embodiments, the chemotherapeutic composition used on the first administration day is the same as or different from the chemotherapeutic composition used on the fourth administration day. In some embodiments, the chemotherapeutic composition used on the first administration day is the same as or different from the chemotherapeutic composition used on the fifth administration day. In some embodiments, the chemotherapeutic composition used on the first administration day is the same as or different from the chemotherapeutic composition used on the sixth administration day. In some embodiments, the chemotherapeutic composition used on the first administration day is the same as or different from the chemotherapeutic composition used on the seventh administration day.

In some embodiments, the treatment schedule includes administration of a chemotherapeutic agent or chemotherapeutic composition (e.g., the first, the second, the third, the fourth, the fifth, the sixth, the seventh, or the eighth) once every 3 weeks. In some embodiments, the treatment schedule includes administration of a chemotherapeutic agent or chemotherapeutic composition once every 1 week, 2 weeks, 3 weeks, 4 weeks, 5 weeks, 6 weeks, 7 weeks, or 8 weeks. In some embodiments, the treatment schedule includes administration of a chemotherapeutic agent or chemotherapeutic composition two times every 1 week, 2 weeks, 3 weeks, 4 weeks, 5 weeks, 6 weeks, 7 weeks, or 8 weeks. In some embodiments, the treatment schedule includes administration of a chemotherapeutic agent or chemotherapeutic composition once every 1 week in a treatment cycle of 1 week, 2 weeks, 3 weeks, 4 weeks, 5 weeks, 6 weeks, 7 weeks, or 8 weeks. In some embodiments, the treatment schedule includes administration of a chemotherapeutic agent or chemotherapeutic composition twice every 1 week in a treatment cycle of 1 week, 2 weeks, 3 weeks, 4 weeks, 5 weeks, 6 weeks, 7 weeks, or 8 weeks. In some embodiments, the treatment schedule includes administration of a chemotherapeutic agent or chemotherapeutic composition three times (e.g., day 1, 2, 3, or day 1, 3, 5) every week in a treatment cycle of 1 week, 2 weeks, 3 weeks, 4 weeks, 5 weeks, 6 weeks, 7 weeks, or 8 weeks. In some embodiments, the treatment schedule includes administration of a chemotherapeutic agent or chemotherapeutic composition day 1, day 8, and day 15 of a 21-day treatment cycle. The chemotherapeutic composition described herein can independently be the first, second, third, fourth, fifth, sixth, seventh, or eighth chemotherapeutic composition. In some embodiments, the treatment schedule includes administration of a chemotherapeutic agent or chemotherapeutic composition every day of the week for a week. In some embodiments, the treatment schedule includes administration of a chemotherapeutic agent or chemotherapeutic composition every day of the week for 2 weeks, 3 weeks, or 4 weeks. In some embodiments, the treatment schedule includes administration of a chemotherapeutic agent or chemotherapeutic composition on day 1 in weekly treatment. In some embodiments, the treatment schedule includes administration of a chemotherapeutic agent or chemotherapeutic composition on day 1 and day 2 in weekly treatment. In some embodiments the treatment schedule includes administration of a chemotherapeutic agent or chemotherapeutic composition on day 1, day 2, and day 3 in weekly treatment. In some embodiments, the treatment schedule includes administration of a chemotherapeutic agent or chemotherapeutic composition on day 1, day 3, day 5 in weekly treatment. In some embodiments, the treatment schedule includes administration of a chemotherapeutic agent or chemotherapeutic composition on day 1, day 2, day 3, and day 4 in weekly treatment. In some embodiments, the treatment schedule includes administration of a chemotherapeutic agent or chemotherapeutic composition on day 1, day 2, day 3, day 4, and day 5 in weekly treatment. The treatment schedule includes administration of a chemotherapeutic agent or chemotherapeutic composition on day 1, day 2, day 3, day 4, day 5, and day 6 in weekly treatment.

In some embodiments, the treatment schedule includes administration of plinabulin once every 3 weeks. In some embodiments, the treatment schedule includes administration of plinabulin once every 1 week, 2 weeks, 3 weeks, 4 weeks, 5 weeks, 6 weeks, 7 weeks, or 8 weeks. In some embodiments, the treatment schedule includes administration of plinabulin two times every 1 week, 2 weeks, 3 weeks, 4 weeks, 5 weeks, 6 weeks, 7 weeks, or 8 weeks. In some embodiments, the treatment schedule includes administration of plinabulin once every 1 week in a treatment cycle of 1 week, 2 weeks, 3 weeks, 4 weeks, 5 weeks, 6 weeks, 7 weeks, or 8 weeks. In some embodiments, the treatment schedule includes administration of plinabulin twice every 1 week in a treatment cycle of 1 week, 2 weeks, 3 weeks, 4 weeks, 5 weeks, 6 weeks, 7 weeks, or 8 weeks. In some embodiments, the treatment schedule includes administration of plinabulin three times (e.g., day 1, 2, 3, or day 1, 3, 5) every 1 week in a treatment cycle of 1 week, 2 weeks, 3 weeks, 4 weeks, 5 weeks, 6 weeks, 7 weeks, or 8 weeks. In some embodiments, the treatment schedule includes administration of plinabulin day 1, day 8, and day 15 of a 21-day treatment cycle. The chemotherapeutic composition described herein can independently be the first, second, third, fourth, fifth, sixth, seventh, or eighth chemotherapeutic composition. In some embodiments, the treatment schedule includes administration of plinabulin every day of the week for a week. In some embodiments, the treatment schedule includes administration of plinabulin every day of the week for 2 weeks, 3 weeks, or 4 weeks. In some embodiments, the treatment schedule includes administration of plinabulin on day 1 in weekly treatment. In some embodiments, the treatment schedule includes administration of plinabulin on day 1 and day 2 in weekly treatment. In some embodiments the treatment schedule includes administration of plinabulin on day 1, day 2, and day 3 in weekly treatment. In some embodiments, the treatment schedule includes administration of plinabulin on day 1, day 3, day 5 in weekly treatment. In some embodiments, the treatment schedule includes administration of plinabulin on day 1, day 2, day 3, and day 4 in weekly treatment. In some embodiments, the treatment schedule includes administration of plinabulin on day 1, day 2, day 3, day 4, and day 5 in weekly treatment. the treatment schedule includes administration of plinabulin on day 1, day 2, day 3, day 4, day 5, and day 6 in weekly treatment. In some embodiments, the treatment schedule includes administration of plinabulin on day 1 in a 21 day treatment cycle about 30 mins after the administration of the chemotherapeutic agent.

The treatment cycle can be repeated as long as the regimen is clinically tolerated. In some embodiments, the treatment cycle for the chemotherapeutic agent and plinabulin is repeated for n times, wherein n is an integer in the range of 2 to 30. In some embodiments, n is 2, 3, 4, 5, 6, 7, 8, 9, or 10. In some embodiments, a new treatment cycle can occur immediately after the completion of the previous treatment cycle. In some embodiments, a new treatment cycle can occur a period of time after the completion of the previous treatment cycle. In some embodiments, a new treatment cycle can occur after 1 week, 2 weeks, 3 weeks, 4 weeks, 5 weeks, 6 weeks, or 7 weeks after the completion of the previous treatment cycle.

In some embodiments, the use of plinabulin can reduce the incidence of thrombocytopenia (e.g., Grade 1, 2, 3 or 4) by at least about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, or 100%. In some embodiments, the use of plinabulin can reduce the incidence of thrombocytopenia (e.g., Grade 1, 2, 3 or 4) by at least about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, or 100%. In some embodiments, the use of plinabulin can reduce the incidence of thrombocytopenia (e.g., Grade 1, 2, 3 or 4) by less than about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, or 100%. In some embodiments, the use of plinabulin can reduce the incidence of thrombocytopenia (e.g., Grade 1, 2, 3 or 4) in the range of about 5%-40%, 10%-40%, 12.5%-40%, 5%-50%, 10%-50%, 12.5%-50%, 15%-50%, 17.5%-50%, 20%-50%, 25%-50%, 27.5%-50%, 30%-50%, 5%-60%, 10%-60%, 12.5%-60%, 15%-60%, 17.5%-60%, 20%-60%, 25%-60%, 27.5%-60%, 30%-60%, 35%-60%, 37.5%-60%, 40%-60%, 45%-70%, or 50%-80%.

Both thrombocytopenia (TP) and ≥30% decrease in platelet count are associated with increased mortality, morbidity, and length of stay (LOS) for patients, as described in *J Pediatr Hematol Oncol*, V33:8 (December 2011), which is incorporated by reference in its entirety. Plinabulin can reduce the incidence of thrombocytopenia by at least 30%. In some embodiments, plinabulin can prevent the platelet count from decreasing for more than 30%. In some embodiments, plinabulin can prevent the platelet count from decreasing for more than 30%. In some embodiments, plinabulin can prevent the platelet count from decreasing for more than 30%. In some embodiments, plinabulin can prevent the platelet count from decreasing for more than 20%. In some embodiments, plinabulin can prevent the platelet count from decreasing for more than 40%. In some embodiments, plinabulin can prevent the platelet count from decreasing for more than 50%.

In some embodiments, the use of plinabulin can be about 10%, 20%, 30%, 40%, 50%, 60%, 70%, 80%, 90%, 100%, 110%, 120%, 130%, 140%, 150%, 160%, 170%, 180%, 190%, 200%, more effective than the use of pegfilgrastim in reducing the incidence of thrombocytopenia (e.g., Grade 1, 2, 3 or 4). In some embodiments, the use of plinabulin can be greater than about 10%, 20%, 30%, 40%, 50%, 60%, 70%, 80%, 90%, 100%, 110%, 120%, 130%, 140%, 150%, 160%, 170%, 180%, 190%, 200%, 225%, 250%, 275%, or 300%, more effective than the use of pegfilgrastim in reducing the incidence of thrombocytopenia (e.g., Grade 1, 2, 3 or 4). In some embodiments, the use of plinabulin can be less than about 10%, 20%, 30%, 40%, 50%, 60%, 70%, 80%, 90%, 100%, 110%, 120%, 130%, 140%, 150%, 160%, 170%, 180%, 190%, 200%, 225%, 250%, 275%, 300%, 350% 400%, 450%, or 500% more effective than the use of pegfilgrastim in reducing the incidence of thrombocytopenia (e.g., Grade 1, 2, 3 or 4). In some embodiments, the use of plinabulin can be greater than about 10%, 20%, 30%, 40%, 50%, 60%, 70%, 80%, 90%, 100%, 110%, 120%, 130%, 140%, 150%, 160%, 170%, 180%, 190%, 200%, 225%, 250%, 275%, 300%, 350% 400%, 450%, or 500% more effective than the use of pegfilgrastim in reducing the incidence of thrombocytopenia (e.g., Grade 1, 2, 3 or 4).

In some embodiments, the use of plinabulin can reduce the duration of thrombocytopenia by about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times. In some embodiments, the use of plinabulin can reduce the duration of thrombocytopenia by greater than about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times. In some embodiments, the use of plinabulin can reduce the duration of thrombocytopenia by less than about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times. In some embodiments, the use of plinabulin can reduce the duration of thrombocytopenia in the range of about 5%-15 times, 20%-10 times, or 50%-500%.

For patients who receive gemcitabine treatment, in some embodiments, the use of plinabulin can lead to an increase of platelet count by about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times faster. For patients who receive gemcitabine treatment, in some embodiments, the use of plinabulin can lead to an increase of platelet count at least about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times faster. For patients who receive gemcitabine treatment, in some embodiments, the use of plinabulin can lead to an increase of platelet count less than about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times. For patients who receive gemcitabine treatment, in some embodiments, the use of plinabulin can lead to an increase of platelet count in the range of about 5%-15 times, 20%-10 times, or 50%-500%.

In some embodiments, plinabulin can be about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times more effective than G-CSF (e.g., pegfilgrastim or filgrastim) in reducing the duration of thrombocytopenia. In some embodiments, plinabulin can be greater than about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times more effective than G-CSF (e.g., pegfilgrastim or filgrastim) in reducing the duration of thrombocytopenia. In some embodiments, plinabulin can be less than about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times more effective than G-CSF (e.g., pegfilgrastim or filgrastim) in reducing the duration of thrombocytopenia. In some embodiments, plinabulin can be in the range of about 5%-15 times, 20%-10 times, or 50%-500% more effective than G-CSF (e.g., pegfilgrastim or filgrastim) in reducing the duration of thrombocytopenia.

The administration period can be a multi-week treatment cycle as long as the tumor remains under control and the regimen is clinically tolerated. In some embodiments, a single dosage of Plinabulin or other therapeutic agent can be administered once a week, and preferably once on each of day 1 and day 8 of a three-week (21 day) treatment cycle. In some embodiments, a single dosage of Plinabulin or other therapeutic agent can be administered once a week, twice a week, three times per week, four times per week, five times per week, six times per week, or daily during a one-week, two-week, three-week, four-week, or five-week treatment cycle. The administration can be on the same or different day of each week in the treatment cycle.

The treatment cycle can be repeated as long as the regimen is clinically tolerated. In some embodiments, the treatment cycle is repeated for n times, wherein n is an integer in the range of 2 to 30. In some embodiments, n is 2, 3, 4, 5, 6, 7, 8, 9, or 10. In some embodiments, a new treatment cycle can occur immediately after the completion of the previous treatment cycle. In some embodiments, a new treatment cycle can occur a period of time after the completion of the previous treatment cycle.

Administration of the pharmaceutical compositions described herein can be via any of the accepted modes of administration for agents that serve similar utilities including, but not limited to, orally, sublingually, buccally, subcutaneously, intravenously, intranasally, topically, transdermally, intradermally, intraperitoneally, intramuscularly, intrapulmonarilly, vaginally, rectally, or intraocularly. Oral and parenteral administrations are customary in treating the indications that are the subject of the preferred embodiments.

Some embodiments relate to a method of reducing thrombocytopenia in a subject, comprising administering plinabulin or a pharmaceutically acceptable salt thereof to a subject in need thereof. In some embodiments, the thrombocytopenia is chemotherapy-induced. In some embodiments, the thrombocytopenia is induced by administration of a chemotherapeutic composition. The chemotherapeutic composition can include one or more chemotherapeutic agents. In some embodiments, the chemotherapeutic agent is a nucleoside analog. In some embodiments, the chemotherapeutic agent is gemcitabine.

In some embodiments, the thrombocytopenia is induced by radiation therapy. Some embodiments include reducing the likelihood of onset of, or reducing the severity of, thrombocytopenia in a subject, comprising administering plinabulin to a subject in need thereof.

Some embodiments of the foregoing methods comprise administering plinabulin or a pharmaceutically acceptable salt thereof and one or more additional chemotherapeutic agents. In various embodiments, the additional chemotherapeutic agent is selected from the group consisting of cyclophosphamide, doxorubicin, paclitaxel, carboplatin, cisplatin, irinotecan, topotecan, and pharmaceutically acceptable salts thereof, or combinations of two or more of the foregoing, or combinations of one or more of the foregoing and docetaxel. In one embodiment, plinabulin and the one or more additional chemotherapeutic agent are administered simultaneously. In one such embodiment, administration in combination is accomplished by combining the agents in a single dosage form. In another embodiment, the agents are administered sequentially. In one embodiment the agents are administered through the same route, such as orally or intravenously. In another embodiment, the agents are administered through different routes, such as one being administered orally and another being administered i.v. In some embodiments, the time period between administration of one or more agent and administration of the co-administered one or more agent can be about 1 hour, 2 hours, 3 hours, 5 hours, 8 hours, 10 hours, 12 hours, 15 hours, 18 hours, 20 hours, 24 hours, 36 hours, 48 hours, 3 days, 4 days, 5 days, 6 days, 7 days, 10 days, 14 days, 21 days, 28 days, or 30 days. In some embodiments, plinabulin is administered prior to administration of the one or more additional chemotherapeutic agents. In other embodiments, the additional chemotherapeutic agents are administered prior to plinabulin.

In some embodiments, the method described herein comprises co-administering one or more chemotherapeutic agents and plinabulin. In some embodiments, the method described herein comprises co-administering two chemotherapeutic agents and plinabulin. In some embodiments, the method described herein comprises co-administering three chemotherapeutic agents and plinabulin. In some embodiments, the method described herein comprises co-administering four chemotherapeutic agents and plinabulin. For embodiments wherein plinabulin is administered with one or more chemotherapeutic agents or chemotherapeutic composition, G-CSF can also be administered to the patient in combination with plinabulin.

In some embodiments, when a second and/or third chemotherapeutic agents are administered with the first chemotherapeutic agent and plinabulin, the second or third chemotherapeutic agent can be administered prior to, after, or concurrently with the coadministration of the first chemotherapeutic agent and plinabulin. In some embodiments, the administration schedule of the second or third chemotherapeutic agent can be different from the first chemotherapeutic agent. In some embodiments, the administration schedule of the second or third chemotherapeutic agent can be the same as the first chemotherapeutic agent.

In some embodiments, the additional chemotherapeutic agent does not include docetaxel. In some embodiments, the additional chemotherapeutic agent does not include a taxane.

Some embodiments comprise administering plinabulin or a pharmaceutically acceptable salt thereof and radiation therapy to a subject.

Some embodiments comprise administering plinabulin or a pharmaceutically acceptable salt thereof, G-CSF, and radiation therapy to a subject. In some embodiments, the patient also receives platelet transfusion. In some embodiments, the method described herein also include administering G-CSF. In some embodiments, the method described herein does not include administering G-CSF.

Some embodiments include identifying that a subject is suffering from thrombocytopenia and then administering plinabulin or a pharmaceutically acceptable salt thereof to the subject. Other embodiments include administrating plinabulin or a pharmaceutically acceptable salt thereof to a subject before detection of thrombocytopenia to reduce the incidence or severity thereof. For example, some embodiments include identifying a subject that is at risk for developing thrombocytopenia (e.g., due to myelosuppressive chemotherapy or radiation therapy) but does not yet exhibit thrombocytopenia, and then administering plinabulin or a pharmaceutically acceptable salt thereof to the subject.

In some embodiments, plinabulin can be used together with G-CSF to reduce, ameliorate, or prevent thrombocytopenia caused by a chemotherapeutic agent or chemotherapeutic composition or radiation therapy.

In some embodiments of the foregoing methods, an additional agent that acts to reduce thrombocytopenia are also administered. For example, in some embodiments, the methods are practiced without administering a G-CSF (e.g., pegfilgrastim or filgrastim). In some embodiments, the methods are practiced without administering any additional active agent beyond the agents recited in above.

In some of the foregoing embodiments, the subject is a human.

In some embodiments, the methods described above can be achieved by administering plinabulin and any additional chemotherapeutic agents via any of the accepted modes of administration for agents that serve similar utilities including, but not limited to, orally, sublingually, buccally, subcutaneously, intravenously, intranasally, topically, transdermally, intradermally, intraperitoneally, intramuscularly, intrapulmonarilly, vaginally, rectally, or intraocularly. Oral and parenteral administrations are customary in treating the indications that are the subject of the preferred embodiments.

The administration period can be a multi-week treatment cycle. In some embodiments, a single dosage of Plinabulin or other therapeutic agent can be administered once a week, and preferably once on each of day 1 and day 8 of a three-week (21 day) treatment cycle. In some embodiments, a single dosage of Plinabulin or other therapeutic agent can be administered once a week, twice a week, three times per week, four times per week, five times per week, six times per week, or daily during a one-week, two-week, three-week, four-week, or five-week treatment cycle. The administration can be on the same or different day of each week in the treatment cycle.

The treatment cycle can be repeated as long as the regimen is clinically tolerated. In some embodiments, the treatment cycle is repeated for n times, wherein n is an integer in the range of 2 to 30. In some embodiments, n is 2, 3, 4, 5, 6, 7, 8, 9, or 10. In some embodiments, a new treatment cycle can occur immediately after the completion of the previous treatment cycle. In some embodiments, a new treatment cycle can occur a period of time after the completion of the previous treatment cycle.

Pharmaceutical Compositions

Some embodiments include pharmaceutical compositions comprising plinabulin or a pharmaceutically effective salt thereof and an additional chemotherapeutic agent. In various embodiments, the additional chemotherapeutic agent is selected from the group consisting of methotrexate, vinblastine, doxorubicin, cisplatin, MVAC (methotrexate, vinblastine, doxorubicin and cisplatin), docetaxel, trastuzumab, cyclophosphamide, paclitaxel, dose-dense AC followed by T (i.e., doxorubicin, cyclophosphamide, paclitaxel), TAC (docetaxel, doxorubicin, cyclophosphamide), fluorouracil, bleomycin, etoposide, vincristine, procarbazine, prednisone, BEACOPP (bleomycin, etoposide, doxorubicin, cyclophosphamide, vincristine, procarbazine, prednisone), gemcitabine, ifosfamide, carboplatin, ICE (ifosfamide, carboplatin, etoposide), rituximab, RICE (rituximab, ifosfamide, carboplatin, etoposide), CHOP-14 (cyclophosphamide, doxorubicin, vincristine, prednisone), mesna, novantrone, MINE (mesna, ifosfamide, novantrone, etoposide), dexamethasone, cytarabine DHAP (dexamethasone, cisplatin, cytarabine), methylprednisolone, ESHAP (etoposide, methylprednisolone, cisplatin, cytarabine), HyperCVAD and rituximab (cyclophosphamide, vincristine, doxorubicin, dexamethasone, rituximab), dacarbazine, vinblastine, dacarbazine-based combination (dacarbazine, cisplatin, vinblastine), dacarbazine-based combination with IL-2 and interferon alfa (dacarbazine, cisplatin, vinblastine, IL-2, interferon alfa), topotecan, MAID (mesna, doxorubicin, ifosfamine, dacarbazine), VeIP (vinblastine, ifosfamide, cisplatin), VIP (etoposide, ifosfamide, cisplatin), TIP (paclitaxel, ifosfamide, cisplatin), gemcitabine, CMF classic (cyclophosphamide, methotrexate, fluorouracil), AC (doxorubicin, cyclophosphamide), FEC (fluorouracil, epirubicin, cyclophosphamide), TC (docetaxel, cyclophosphamide), cisplatin/topotecan, paclitaxel/cisplatin, irincotecan, FOLFOX (fluorouracil, leucovorin, oxaliplatin), irincotecan/cisplatin, epirubicin/cisplatin/5-fluorouracil, epirubicin/cisplatin/capecitabine, DT-PACE (dexamethasone/thalidomide/cisplatin/doxorubicin/cyclophosphamide/etoposide), ET-PACE and bortezomib, EPOCH (etoposide, prednisone, vincristine, cyclophosphamide, doxorubicin), GDP (gemcitabine, dexamethasone, cisplatin), GDP and rituximab, FMR (fludarabine, mitoxantrone, rituximab, CHOP and rituximab (cyclophosphamide, doxorubicin, vincristine, prednisone, rituximab), cisplatin/paclitaxel, cisplatin/vinorelbine, cisplatin/docetaxel, ciaplatin/etoposide, carboplatin/paclitaxel, carboplatin/docetaxel, FOLFIRINOX (5-FU/leucovorin, irinotecan and oxaliplatin), cabazitaxel, etoposide/carboplatin, etoposide/cisplatin. In some embodiments, the one or more additional chemotherapeutic compositions (e.g., the second, third, fourth, fifth, sixth, seventh, or eighth chemotherapeutic composition) can independently include one or more agents selected from the group consisting of methotrexate, vinblastine, doxorubicin, cisplatin, docetaxel, trastuzumab, cyclophosphamide, paclitaxel, fluorouracil, bleomycin, etoposide, vincristine, procarbazine, prednisone, gemcitabine, ifosfamide, carboplatin, mesna, novantrone, cytarabine methylprednisolone, rituximab dacarbazine, vinblastine, topotecan, gemcitabine, irincotecan, epirubicin, 5-fluorouracil, capecitabine, bortezomib, and cabazitaxel.

In some embodiments, the first chemotherapeutic composition can include one or more agents selected from the group consisting of methotrexate, vinblastine, doxorubicin, cisplatin, MVAC (methotrexate, vinblastine, doxorubicin and cisplatin), trastuzumab, cyclophosphamide, dose-dense AC followed by T (i.e., doxorubicin, cyclophosphamide, paclitaxel), fluorouracil, bleomycin, etoposide, vincristine, procarbazine, prednisone, BEACOPP (bleomycin, etoposide, doxorubicin, cyclophosphamide, vincristine, procarbazine, prednisone), gemcitabine, ifosfamide, carboplatin, ICE (ifosfamide, carboplatin, etoposide), rituximab, RICE (rituximab, ifosfamide, carboplatin, etoposide), CHOP-14 (cyclophosphamide, doxorubicin, vincristine, prednisone), mesna, novantrone, MINE (mesna, ifosfamide, novantrone, etoposide), dexamethasone, cytarabine DHAP (dexamethasone, cisplatin, cytarabine), methylprednisolone, ESHAP (etoposide, methylprednisolone, cisplatin, cytarabine), HyperCVAD and rituximab (cyclophosphamide, vincristine, doxorubicin, dexamethasone, rituximab), dacarbazine, vinblastine, dacarbazine-based combination (dacarbazine, cisplatin, vinblastine), dacarbazine-based combination with IL-2 and interferon alfa (dacarbazine, cisplatin, vinblastine, IL-2, interferon alfa), topotecan, MAID (mesna, doxorubicin, ifosfamine, dacarbazine), VeIP (vinblastine, ifosfamide, cisplatin), VIP (etoposide, ifosfamide, cisplatin), TIP (paclitaxel, ifosfamide, cisplatin). In some embodiments, the gemcitabine, CMF classic (cyclophosphamide, methotrexate, fluorouracil), AC (doxorubicin, cyclophosphamide), FEC (fluorouracil, epirubicin, cyclophosphamide), cisplatin/topotecan, paclitaxel/cisplatin, irincotecan, FOLFOX (fluorouracil, leucovorin, oxaliplatin), irincotecan/cisplatin, epirubicin/cisplatin/5-fluorouracil, epirubicin/cisplatin/capecitabine, DT-PACE (dexamethasone/thalidomide/cisplatin/doxorubicin/cyclophosphamide/etoposide), ET-PACE and bortezomib, EPOCH (etoposide, prednisone, vincristine, cyclophosphamide, doxorubicin), GDP (gemcitabine, dexamethasone, cisplatin), GDP and rituximab, FMR (fludarabine, mitoxantrone, rituximab, CHOP and rituximab (cyclophosphamide, doxorubicin, vincristine, prednisone, rituximab), cisplatin/paclitaxel, cisplatin/vinorelbine, ciaplatin/etoposide, carboplatin/paclitaxel, FOLFIRINOX (5-FU/leucovorin, irinotecan and oxaliplatin), cabazitaxel, etoposide/carboplatin, etoposide/cisplatin. In some embodiments, the first chemotherapeutic compositions can include one or more agents selected from the group consisting of methotrexate, vinblastine, doxorubicin, cisplatin, trastuzumab, cyclophosphamide, fluorouracil, bleomycin, etoposide, vincristine, procarbazine, prednisone, gemcitabine, ifosfamide, carboplatin, mesna, novantrone, cytarabine methylprednisolone, rituximab dacarbazine, vinblastine, topotecan, gemcitabine, irincotecan, epirubicin, 5-fluorouracil, capecitabine, and bortezomib.

In some embodiments, the pharmaceutical compositions described above comprise an additional agent that acts to reduce thrombocytopenia. For example, in some embodiments, the pharmaceutical compositions include a granulocyte-colony stimulating factor (e.g., pegfilgrastim or filgrastim). Examples of granulocyte-colony stimulating factor drug include but are not limited to Neupogen® (Amgen), Tevagrastim® (Teva), Biograstim® (CT Arzneimittel), Ratiograstim® (Ratiopharm GmbH)), Zarxio® (Sandoz GmbH), Filgrastim Hexal® (Hexal AG), Neulasta® (Amgen), Granocyte® and Neutrogin® (Chugai), and Neu-Up® (Kyowa Hakko), Rolontis® (Spectrum, eflapegrastim), Aiduo (mecapegfilgrastim, Hengrui).

In some embodiments, the pharmaceutical compositions described above do not comprise any additional agent that acts to reduce thrombocytopenia. For example, in some embodiments, the pharmaceutical compositions do not include a granulocyte-colony stimulating factor (e.g., pegfilgrastim or filgrastim). In some embodiments, the pharmaceutical compositions do not include any additional active agent beyond the agents recited in the compositions above.

Other embodiments include two or more separate pharmaceutical compositions, one of which comprises plinabulin or a pharmaceutically acceptable salt thereof, and one or more other pharmaceutical compositions that comprise additional chemotherapeutic agents. In various embodiments, the additional chemotherapeutic agent is selected from the group consisting of cyclophosphamide, doxorubicin, paclitaxel, carboplatin, cisplatin, irinotecan, and pharmaceutically acceptable salts thereof.

In some embodiments, the compositions described above can further include one or more pharmaceutically acceptable diluents. In some embodiments, the pharmaceutically acceptable diluent can include Kolliphor® (Polyethylene glycol (15)-hydroxystearate). In some embodiments, the pharmaceutically acceptable diluent can include propylene glycol. In some embodiments, the pharmaceutically acceptable diluents can include Kolliphor® and propylene glycol. In some embodiments, the pharmaceutically acceptable diluents can include Kolliphor® and propylene glycol, wherein the Kolliphor® is about 40% by weight and propylene glycol is about 60% by weight based on the total weight of the diluents. In some embodiments, the composition can further include one or more other pharmaceutically acceptable excipients.

In some embodiments, the compositions described above can further include one or more pharmaceutically acceptable carrier or excipient. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The compositions described herein are preferably provided in unit dosage form. As used herein, a "unit dosage form" is a composition containing an amount of a compound or composition that is suitable for administration to an animal, preferably a mammalian subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, although a single administration is not specifically excluded. The skilled artisan will recognize that the formulation does not specifically contemplate the entire course of therapy and such decisions are left for those skilled in the art of treatment rather than formulation.

Standard pharmaceutical formulation techniques can be used to make the pharmaceutical compositions described herein, such as those disclosed in Remington's The Science and Practice of Pharmacy, 21st Ed., Lippincott Williams & Wilkins (2005), incorporated herein by reference in its entirety.

The compositions as described above may be in any of a variety of suitable forms for a variety of routes for administration, for example, for oral, sublingual, buccal, nasal, rectal, topical (including transdermal and intradermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the activity of the compound or composition. The amount of carrier employed in conjunction with the compound or composition is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules (e.g., liquid gel capsule and solid gel capsule), granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject composition is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort may be maximized as much as possible, although sometimes formulation considerations (e.g. drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. Ophthalmic solutions may preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

Ophthalmically acceptable antioxidants include, but are not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium (EDTA), although other chelating agents may also be used in place or in conjunction with it.

For topical use, creams, ointments, gels, solutions or suspensions, etc., containing the composition disclosed herein are employed. Topical formulations may generally be comprised of a pharmaceutical carrier, co-solvent, emulsifier, penetration enhancer, preservative system, and emollient.

For intravenous administration, the compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one or more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan. In some embodiments, a single dose of Plinabulin or other therapeutic agent may be from about 5 mg/m$^2$ to about 150 mg/m$^2$ of body surface area, from about 5 mg/m$^2$ to about 100 mg/m$^2$ of body surface area, from about 10 mg/m$^2$ to about 100 mg/m$^2$ of body surface area, from about 10 mg/m$^2$ to about 80 mg/m$^2$ of body surface area, from about 10 mg/m$^2$ to about 50 mg/m$^2$ of body surface area, from about 10 mg/m$^2$ to about 40 mg/m² of body surface area, from about 10 mg/m² to about 30 mg/m² of body surface area, from about 13.5 mg/m² to about 100 mg/m² of body surface area, from about 13.5 mg/m² to about 80 mg/m² of body surface area, from about 13.5 mg/m² to about 50 mg/m² of body surface area, from about 13.5 mg/m² to about 40 mg/m² of body surface area, from about 13.5 mg/m² to about 30 mg/m² of body surface area, from about 15 mg/m² to about 80 mg/m² of body surface area, from about 15 mg/m² to about 50 mg/m² of body surface area, or from about 15 mg/m² to about 30 mg/m² of body surface area. In some embodiments, a single dose of Plinabulin or other therapeutic agent may be from about 13.5 mg/m² to about 30 mg/m² of body surface area. In some embodiments, a single dose of Plinabulin or other therapeutic agent may be about 5 mg/m², about 10 mg/m², about 12.5 mg/m², about 13.5 mg/m², about 15 mg/m², about 17.5 mg/m², about 20 mg/m², about 22.5 mg/m², about 25 mg/m², about 27.5 mg/m², about 30 mg/m², about 40 mg/m², about 50 mg/m², about 60 mg/m², about 70 mg/m², about 80 mg/m², about 90 mg/m², or about 100 mg/m², of body surface area.

In some embodiments, a single dose of Plinabulin or other therapeutic agent may be from about 5 mg to about 300 mg, from about 5 mg to about 200 mg, from about 7.5 mg to about 200 mg, from about 10 mg to about 100 mg, from about 15 mg to about 100 mg, from about 20 mg to about 100 mg, from about 30 mg to about 100 mg, from about 40 mg to about 100 mg, from about 10 mg to about 80 mg, from about 15 mg to about 80 mg, from about 20 mg to about 80 mg, from about 30 mg to about 80 mg, from about 40 mg to about 80 mg, from about 10 mg to about 60 mg, from about 15 mg to about 60 mg, from about 20 mg to about 60 mg, from about 30 mg to about 60 mg, or from about 40 mg to about 60 mg, In some embodiments, a single dose of Plinabulin or other therapeutic agent may be from about 20 mg to about 60 mg, from about 27 mg to about 60 mg, from about 20 mg to about 45 mg, or from about 27 mg to about 45 mg. In some embodiments, a single dose of Plinabulin or other therapeutic agent may be about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg.

In some embodiments, the compositions described herein can be administered or used in combination with other treatments such as radiation or biologic therapies.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

EXAMPLES

Example 1

The effects of plinabulin on the hematology parameters following changes induced by gemcitabine administration in the rat were evaluated. The four treatment groups and the agents used in each group are listed in table 1. The vehicle was prepared using 7.11% Tween 80 (v/v): 25.5% Propylene glycol (v/v): 67.4% D5W (v/v). D5W is 5% dextrose in water for injection.

TABLE 1

Treatment conditions in the four tested groups

| Gr. | Treatment | Gemcitabine Dose level (mg/kg) | Pegfilgrastim or Plinabulin Dose level (mg/kg) | N |
|---|---|---|---|---|
| 1 | Gemcitabine + Vehicle | 100 | 0 | 8 |
| 2 | Vehicle + Pegfilgrastim | 0 | 0.125 | 8 |
| 3 | Gemcitabine + Plinabulin | 100 | 7.5 | 8 |
| 4 | Gemcitabine + Pegfilgrastim | 100 | 0.125 | 8 |

Plinabulin or Pegfilgrastim were first dissolved in the Tween 80-PG mixture and then diluted with D5W. Test item was dissolved in Tween 80-PG mixture on the day before and stored at RF. D5W was added on the day of dosing to complete the formulation.

Animals were randomized based on body weight and/or absolute neutrophil counts and assigned to groups. Before the initiation of dosing, any assigned animals considered unsuitable for use in the study were replaced by alternate animals obtained from the same shipment and maintained under the same environmental conditions. Each animal was uniquely identified using indelible ink. A minimum acclimation period of 5 days was allowed between animal receipt and the start of treatment in order to accustom the animals to the laboratory environment.

For the lab evaluation, the animal blood was collected by jugular venipuncture. Samples (0.3 mL) were collected in EDTA tubes. Additional blood samples may be obtained (e.g., due to clotting of non-serum samples) if permissible sampling frequency and blood volume are not exceeded. After collection, samples were transferred to Clinical Laboratories for hematology analysis using the Advia and results entered into the Provantis® system.

Administration of Inducing Agent

1. Gemcitabine; Groups 1, 3 and 4
Dosing regimen: Single dosing on Day 1
Intravenously (IV bolus) over ~1 minute at a dose volume of 5 mL/kg.
Group 2 received Vehicle.

2. Pegfilgrastim; Groups 2 and 4
Dosing regimen: Single dosing on Day 2, 24 hours after Gemcitabine
Route of administration: Subcutaneous (SC) injection.
Dose volume: 10 mL/kg, based on the most recent body weight measurement 3. Plinabulin; Group 3
Dosing regimen: Single dosing on Day 1, 1 hr after Gemcitabine
Route of administration: Intra-peritoneal (IP) injection.
Dose volume: 10 mL/kg, based on the most recent body weight measurement
Group 1 received Vehicle.

The dosing time points for groups 1 to 4 include days −3, 1, 2, 3, 4, 5, 6, 7, 8, 9 and 10. Additional blood samples may be obtained (e.g., due to clotting of non-serum samples) if permissible sampling frequency and blood volume are not exceeded. After collection, samples will be transferred to Clinical Laboratories for hematology analysis using the Advia and results entered into the Provantis® system.

The testing results are shown in FIG. 1. Plinabulin reduced the thrombocytopenia observed with gemcitabine alone, platelet counts were always greater 500×10³ cells/μL, indicating that plinabulin helped avoid the fast decrease of platelet count and prevent the development of severe thrombocytopenia. On Days 8 and 9 platelet counts were statistically greater in the gemcitabine and plinabulin group than in the gemcitabine alone group. The recovery from the gemcitabine-induced thrombocytopenia was more rapid in the gemcitabine and plinabulin group than for gemcitabine alone.

Example 2

The effects of plinabulin on the thrombocytopenia is studied in comparison to pegfilgrastim. A phase 2/3, multicenter, randomized, double blind study is performed with plinabulin versus pegfilgrastim in patients with solid tumors receiving docetaxel myelosuppressive chemotherapy is evaluated. The patients are on study for approximately 5 months, including screening, on treatment, and follow-up.

Study design: This is a multicenter, randomized study with an open label phase 2 portion and a double blind phase 3 portion. Approximately 190 patients are enrolled in this study. All patients receive docetaxel at a dose of 75 mg/m².

In Phase 2, only patients with advanced or metastatic NSCLC after failing platinum-based therapy are enrolled. In Phase 3, patients with one of the following diagnosis are enrolled: advanced or metastatic breast cancer, who have failed<5 prior lines of chemotherapy; advanced or metastatic NSCLC who have previously received platinum-based therapy and have either disease progression, are intolerant of platinum-based therapy or, in the opinion of the investigator, would benefit from docetaxel chemotherapy; or hormone refractory (androgen independent) metastatic prostate cancer.

The eligibility of all patients will be determined during a 28-day screening period.

Phase 2 (Open Label): Approximately 40 patients with advanced or metastatic NSCLC are enrolled. Patients are randomly assigned with approximately 10 patients enrolled in each arm, with the arm designation and planned intervention as follows:

Arm 1: Docetaxel (75 mg/m²)+pegfilgrastim (6 mg)
Arm 2: Docetaxel (75 mg/m²)+plinabulin (20 mg/m²)
Arm 3: Docetaxel (75 mg/m²)+plinabulin (10 mg/m²)
Arm 4: Docetaxel (75 mg/m²)+plinabulin (5 mg/m²)

Once the study is temporarily closed to enrollment in phase 2, a PK/PD analysis is performed to determine the RP3D. The PK/PD analysis is done by an independent party at the time 40 patients in Phase 2 have completed at least Cycle 1.

Phase 3 (Double Blind): Phase 3 will not begin until RP3D has been determined based on the phase 2 PK/PD analysis as mentioned above.

The inclusion criteria for phase 3 includes advanced or metastatic breast cancer, who have failed<5 prior lines of chemotherapy (Note that study treatment may be the first chemotherapy treatment for advanced or metastatic cancer); advanced or metastatic NSCLC who have previously received platinum based therapy and have either disease progression, are intolerant of platinum-based therapy, or in the opinion of the investigator, would benefit from docetaxel chemotherapy; hormone refractory (androgen independent) metastatic prostate cancer (HRPC).

A fixed dose of 40 mg has been selected as the RP3D following the Phase 2 PK/PD analysis. Approximately 150 patients are planned to be enrolled in the Phase 3 with one of the following diagnosis: advanced or metastatic breast cancer, who have failed<5 prior lines of chemotherapy; advanced or metastatic NSCLC who have previously received platinum-based therapy and have either disease progression, are intolerant of platinum-based therapy or, in the opinion of the investigator, would benefit from docetaxel chemotherapy; or hormone refractory (androgen independent) metastatic prostate cancer. Each eligible patient are stratified according to his or her tumor type (breast cancer, NSCLC or HRPC) and region (Asia, non-Asia). Patients are randomly assigned within each stratum (diagnosis) with equal probability (1:1 ratio) or 75:75, with the arm designation and planned intervention as follows: Arm 1: Docetaxel (75 mg/m²)+pegfilgrastim (6 mg)+placebo matching plinabulin; Arm 2: Docetaxel (75 mg/m²)+plinabulin (40 mg)+placebo matching pegfilgrastim.

All patients must be pre-medicated with oral corticosteroids such as dexamethasone 16 mg per day (e.g., 8 mg bid) for 3 days starting 1 day prior to docetaxel administration in order to reduce the incidence and severity of fluid retention as well as the severity of hypersensitivity reactions (refer to Taxotere® (Prescribing Information)). For hormone-refractory metastatic prostate cancer, given the concurrent use of prednisone, the recommended premedication regimen is oral dexamethasone 8 mg, at 12 hours, 3 hours and 1 hour before the docetaxel infusion.

Data from all patients receiving the RP3D plinabulin dose in Phase 2 and Phase 3 will not be pooled for assessing the primary and secondary study endpoints, but analyzed separately.

Treatments Administered: Both Phase 2 and Phase 3, Cycles 1 to 4, consist of docetaxel 75 mg/m² administered by intravenous (IV) infusion on Day 1 over 60 minutes (±5 minutes) every 21 days. In the phase 2 portion, on Day 1 of each cycle, 1.5 hours (±10 minutes) after the start time of docetaxel infusion (i.e., approximately 30 minutes after the end of docetaxel infusion), patients assigned to a plinabulin arm (arms 2-4) get a single intravenous infusion of plinabulin at their assigned dose over 30 minutes (±5 minutes). Thus, the wait time between end of docetaxel infusion and start of the plinabulin infusion is approximately 30 minutes. On Day 2 of each cycle, ≥24 hours after completing chemotherapy, patients assigned to pegfilgrastim (arm 1) receive a single dose of pegfilgrastim (6 mg) (subcutaneous injection).

In the phase 3 portion, on Day 1 of each cycle, 1.5 hours (±10 minutes) after the start time of docetaxel infusion (i.e., approximately 30 minutes after the end of docetaxel infusion), patients get a single dose of plinabulin or placebo intravenously over 30 minutes (±5 minutes). On Day 2 of each cycle, ≥24 hours after completing chemotherapy, patients receive a single dose of pegfilgrastim (6 mg) or placebo (subcutaneous injection).

All patients complete a safety follow-up visit 30 days (±2 days) after the last dose of study drug. If, in the opinion of the investigator, the patient will benefit from more than 4 cycles of docetaxel and open label pegfilgrastim, then the fifth cycle will not start until completion of the safety follow-up visit (in this instance, the safety follow-up visit will be Cycle 4 Day 21). Follow-up visits will be required to monitor for ongoing treatment-related AEs. All patients experiencing drug-related toxicities of Grade 2 at the End of Treatment visit should be followed-up at least monthly until the AE(s) resolves to Grade 1, the event is considered to be chronic, or the patient receives other anti-cancer therapy. The method of follow-up assessment will be at the Investigator's discretion (for example, patient site visit or telephone call). All deaths which occur within 30 days of study drug administration regardless of relationship to the study drug must be reported to the Sponsor immediately and within 24 hours of becoming aware of the event.

Laboratory test results (hematology and serum chemistry) are collected via a central laboratory. Safety laboratory tests are required prior to treatment on Day 1 of each cycle and can be collected by a local laboratory; however, all other scheduled blood samples as per the schedule assessments and procedure table must also be obtained for central laboratory assessment. Urinalysis is performed at screening only. CD34+ counts are established through a fluorescence-activated cell sorting (FACS) method.

Duration of Treatment: Patients received treatment with study drug for up to 4 cycles in this study, a treatment cycle is 21 days; thereafter, patients may continue receiving docetaxel and pegfilgrastim at the Investigator's discretion. After completion of 4 cycles, patients completed a safety follow-up visit 30 days (±2 days) after the last dose of study drug. If, in the opinion of the investigator, the patient would benefit from more than 4 cycles of docetaxel and open label pegfilgrastim, then the fifth cycle would not start until completion of the safety follow-up visit (in this instance, the safety follow-up visit will be Cycle 4 Day 21).

Pharmacokinetics: Non-compartmental pharmacokinetic analyses are used to calculate plasma concentrations of plinabulin following doses of 5 mg/m$^2$, 10 mg/m$^2$, and 20 mg/m$^2$ and docetaxel in cycle 1 of the phase 2 portion of the study. Patients in Phase 3 follow the plinabulin and docetaxel PK sampling schedules from Phase 2.

Figure 2:
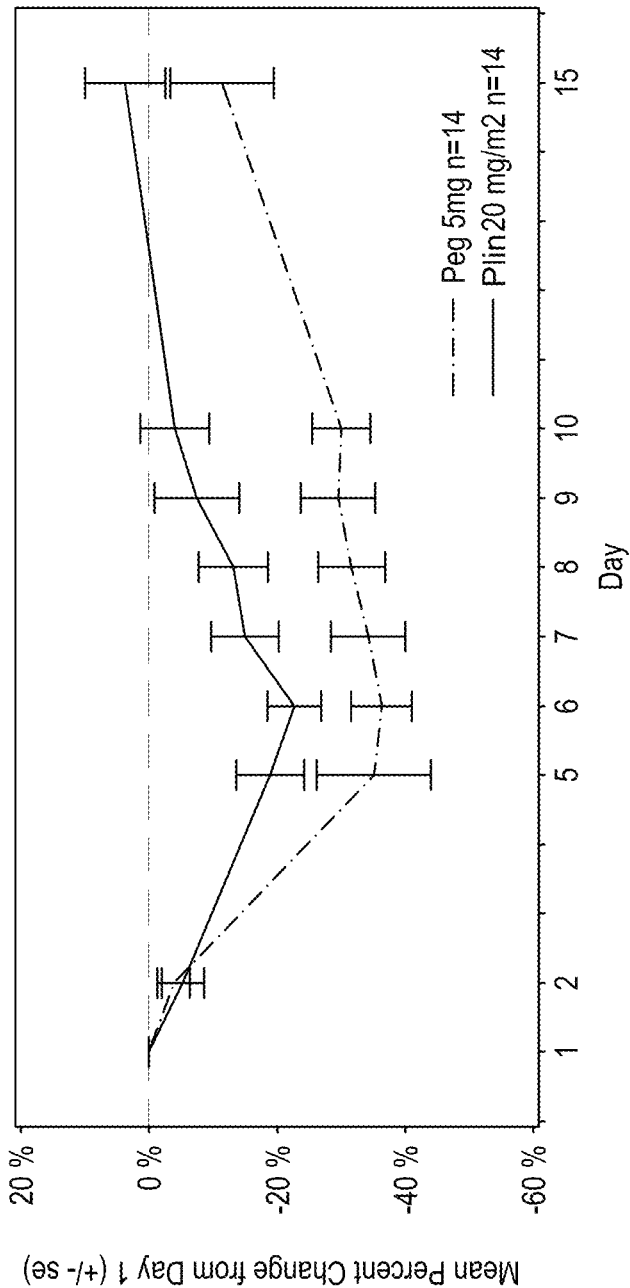
FIG. 2 shows the change of platelet count from day 1 to day 15 for the group administered with 6 mg of pegfilgrastim and the group administered with 20 mg/m$^2$ of plinabulin.
Figure 3:
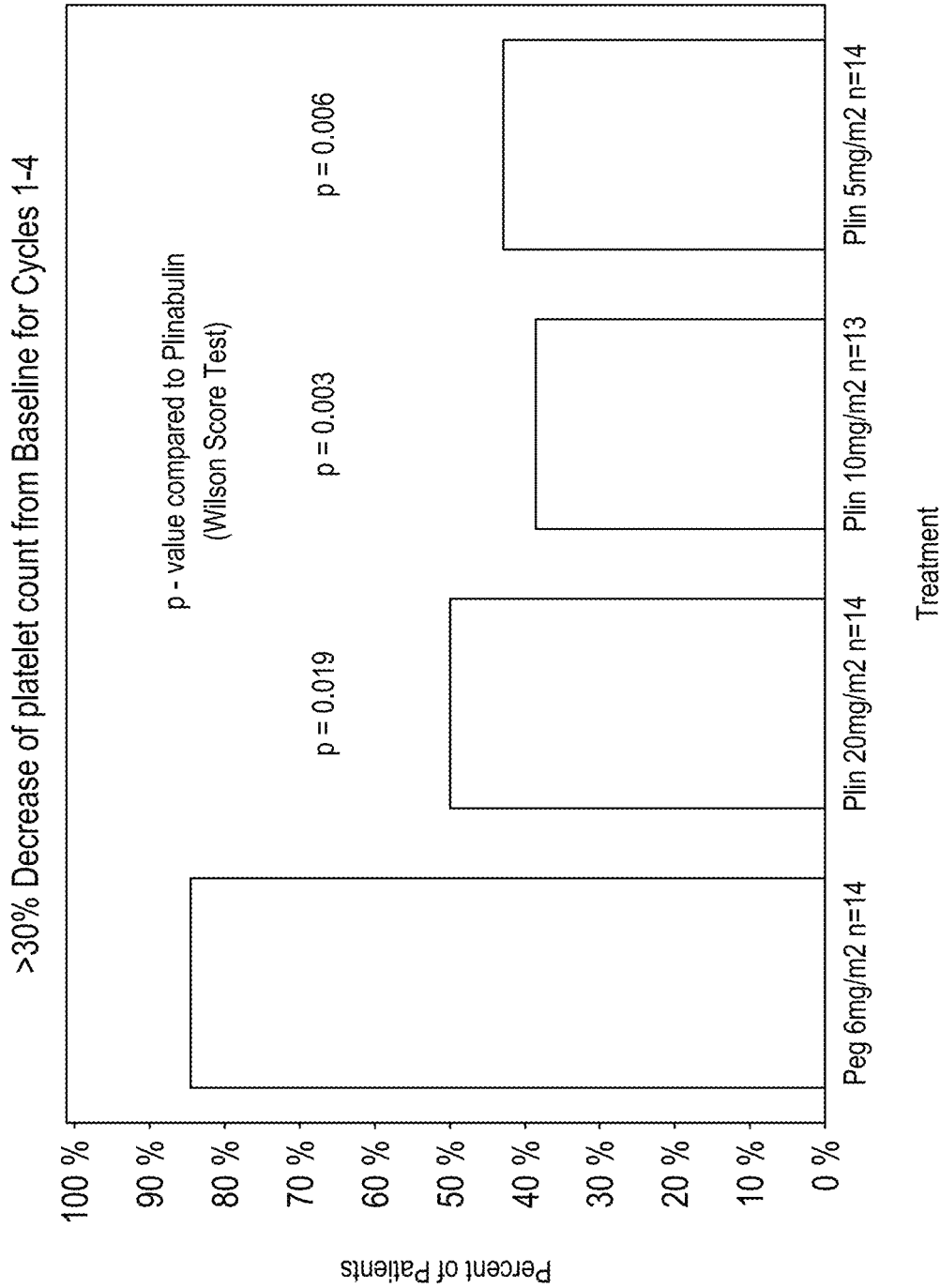
FIG. 3 shows percentage of patients with greater than 30% platelet decrease from baseline in cycles 1-4.
Figure 4:
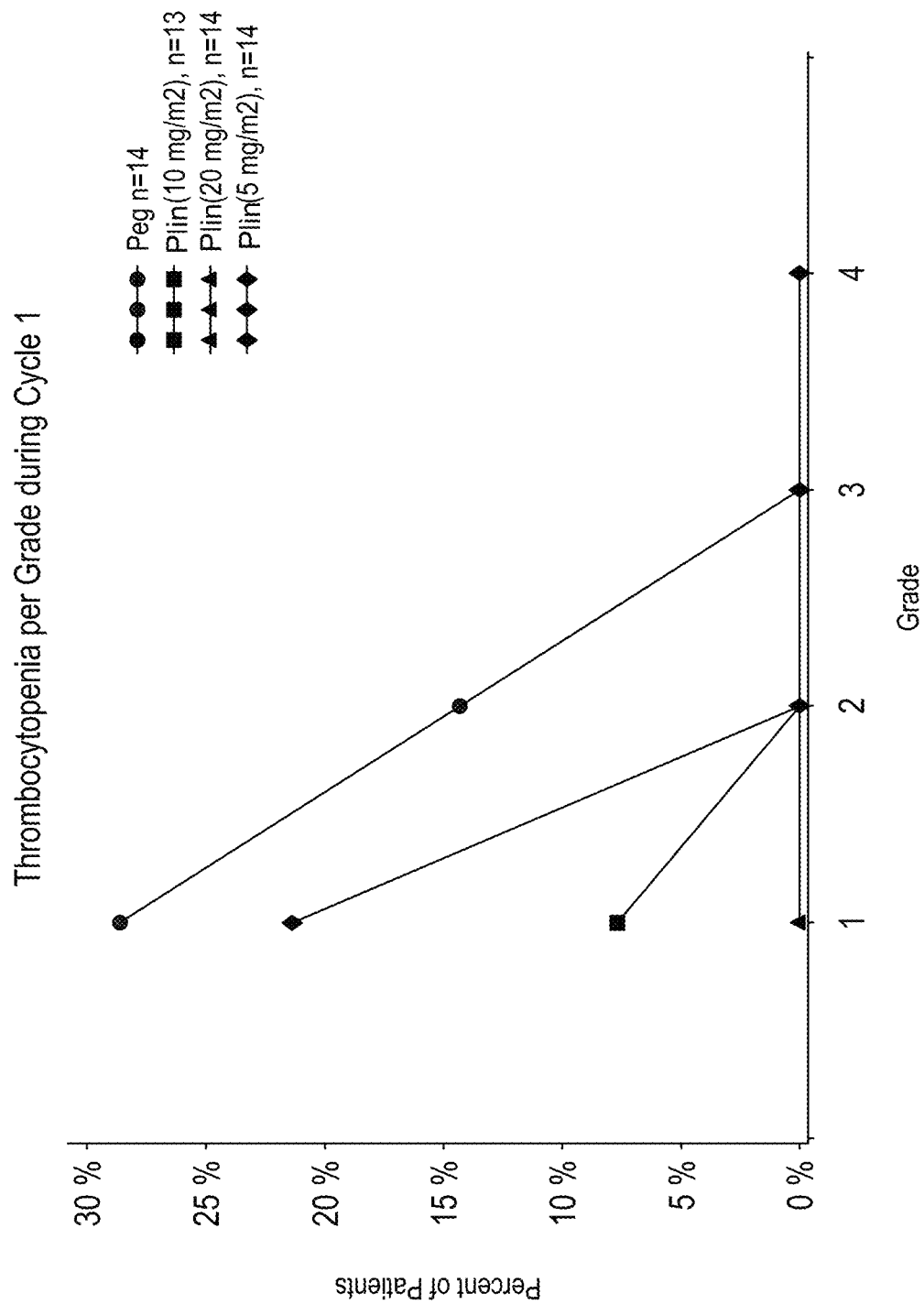
FIG. 4 shows the percentage of patients at each grade of thrombocytopenia for the groups treated with plinabulin at 5, 10 or 20 mg/m$^2$ and the group treated with pegfilgrastim.
Figure 5:
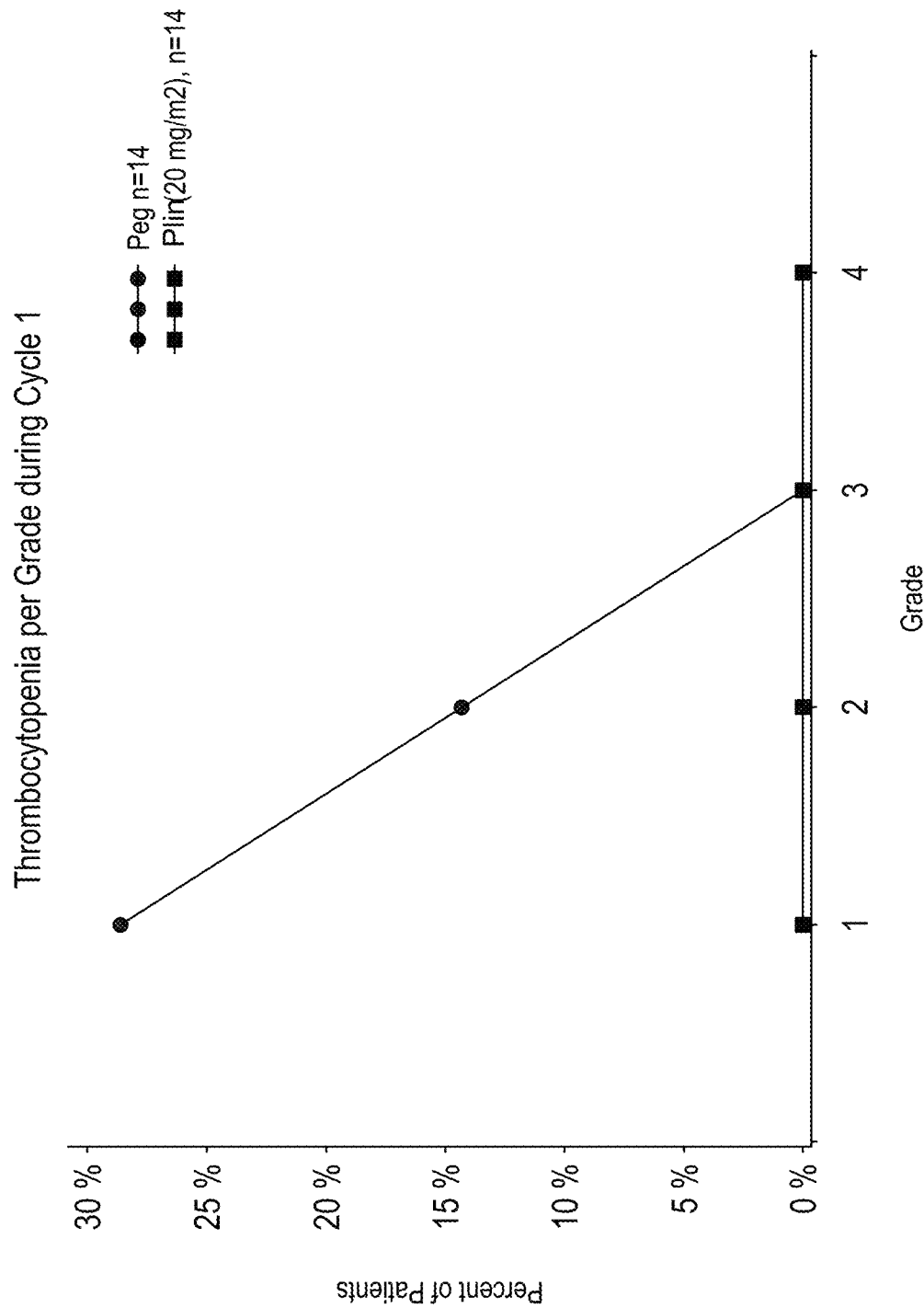
FIG. 5 shows the percentage of patients at each grade of thrombocytopenia for the groups treated with plinabulin 20 mg/m$^2$ and the group treated with pegfilgrastim.

The preliminary results are shown in FIG. 2-4. FIG. 2 shows the change of platelet count from day 1 to day 15 for the group administered with 6 mg of pegfilgrastim and the group administered with 20 mg/m$^2$ of plinabulin; FIG. 3 shows percentage of patients with greater than 30% platelet decrease from baseline in cycles 1-4. FIG. 4 shows the percentage of patients at each grade of thrombocytopenia at 5, 10, 20 mg/m$^2$ plinabulin in comparison with 6 mg pegfilgrastim, and FIG. 5 shows the percentage of patients at each grade of thrombocytopenia for the group administered with 20 mg/m$^2$ of plinabulin and the group administered with 6 mg pegfilgrastim.

In FIG. 2, the change of platelet percentage in the pegfilgrastim group was greater than the plinabulin group, indicating that plinabulin was more effective in maintaining the platelet count in patients undergoing chemotherapy. The difference in the platelet percent change between the two groups is also shown in FIG. 2. FIG. 3 shows that almost 85% patients in the pegfilgrastim group experienced greater than 30% platelet decrease from baseline, while the plinabulin groups showed lower percentages of patients experiencing such a decrease. In FIG. 4, the plinabulin treatment at various dosages (e.g., 5, 10 and 20 mg/m$^2$) showed lower incidences of developing thrombocytopenia than the pegfilgrastim group. In FIG. 5, the patients in the plinabulin group (20 mg/m$^2$) did not develop thrombocytopenia, while some patients in the pegfilgrastim group developed thrombocytopenia. The study results demonstrated that plinabulin was effective in reducing the incidence of thrombocytopenia.

What is claimed is:

1. A method of reducing thrombocytopenia, comprising administering plinabulin or a pharmaceutically acceptable salt thereof to a subject in need thereof, wherein the thrombocytopenia is induced by administration of gemcitabine or a chemotherapeutic composition comprising gemcitabine.

2. The method of claim 1, wherein the subject has a grade 1 thrombocytopenia.

3. The method of claim 1, wherein the subject has a grade 2 thrombocytopenia.

4. The method of claim 1, wherein the subject has a grade 3 thrombocytopenia.

5. The method of claim 1, wherein the subject has a grade 4 thrombocytopenia.

6. The method of claim 1, wherein the plinabulin is administered at a dose in the range of about 2.5 mg/m$^2$ to about 17.5 mg/m$^2$.

7. The method of claim 1, wherein the plinabulin is administered at a dose in the range of about 8.5 mg/m$^2$ to about 32.5 mg/m$^2$.

8. The method of claim 1, wherein the plinabulin is administered at a dose in the range of about 9.5 mg/m$^2$ to about 15.5 mg/m$^2$.

9. The method of claim 1, wherein the plinabulin is administered at a dose in the range of about 15.5 mg/m$^2$ to about 24.5 mg/m$^2$.

10. The method of claim 1, further comprising administering gemcitabine prior to administering plinabulin.

11. The method of claim 10, wherein the gemcitabine is administered about 1 hour prior to plinabulin administration.

12. The method of claim 1, comprising reducing an incidence of a thrombocytopenia by at least 10%.

13. The method of claim 1, comprising reducing an incidence of a thrombocytopenia by at least 30%.

14. The method of claim 1, comprising reducing a duration of a thrombocytopenia by at least 50%.

15. A method of increasing platelet production, stimulating platelet formation, or increasing platelet count in a subject being administered gemcitabine, comprising administering plinabulin or a pharmaceutically acceptable salt thereof to the subject in need thereof.

16. The method of claim 15, wherein the plinabulin is administered at a dose in the range of about 1 mg/m$^2$ to about 50 mg/m$^2$.

17. The method of claim 15, wherein the subject has a grade 1 thrombocytopenia.

18. The method of claim 15, wherein the subject has a grade 2 thrombocytopenia.

19. The method of claim 15, wherein the subject has a grade 3 thrombocytopenia.

20. The method of claim 15, wherein the subject has a grade 4 thrombocytopenia.

21. The method of claim 15, wherein the plinabulin is administered at a dose in the range of about 2.5 mg/m$^2$ to about 17.5 mg/m$^2$.

22. The method of claim 15, wherein the plinabulin is administered at a dose in the range of about 8.5 mg/m$^2$ to about 32.5 mg/m$^2$.

23. The method of claim 15, wherein the plinabulin is administered at a dose in the range of about 9.5 mg/m$^2$ to about 15.5 mg/m$^2$.

24. The method of claim 15, wherein the plinabulin is administered at a dose in the range of about 15.5 mg/m$^2$ to about 24.5 mg/m$^2$.

25. The method of claim 15, wherein the plinabulin is administered at a dose in the range of about 22.5 mg/m$^2$ to about 32.5 mg/m$^2$.

26. The method of claim 15, further comprising administering gemcitabine prior to administering plinabulin.

27. The method of claim 26, wherein the gemcitabine is administered about 1 hour prior to plinabulin administration.

28. The method of claim 15, comprising reducing an incidence of a thrombocytopenia by at least 10%.

29. The method of claim 15, comprising reducing an incidence of a thrombocytopenia by at least 30%.

30. The method of claim 15, comprising reducing a duration of a thrombocytopenia by at least 50%.

31. A method of treating thrombocytopenia, comprising:
  identifying a subject having a breast cancer, ovarian cancer, non-small cell lung cancer, pancreatic cancer, or bladder cancer; and
  administering plinabulin or a pharmaceutically acceptable salt thereof to the subject in need thereof at a dose in the range of about 1 mg/m$^2$ to about 50 mg/m$^2$ to the subject;
  wherein the thrombocytopenia is induced by administration of gemcitabine or a chemotherapeutic composition comprising gemcitabine.

* * * * *